United States Patent [19]

Blondelle et al.

[11] Patent Number: 5,440,016
[45] Date of Patent: Aug. 8, 1995

[54] PEPTIDES OF THE FORMULA (KFMOC) ZZZ AND THEIR USES

[75] Inventors: Sylvie E. Blondelle, La Jolla; Richard A. Houghten, Del Mar, both of Calif.

[73] Assignee: Torrey Pines Institute for Molecular Studies, San Diego, Calif.

[21] Appl. No.: 79,445

[22] Filed: Jun. 18, 1993

[51] Int. Cl.$^6$ ............................................. A61K 38/07
[52] U.S. Cl. .................................... 530/330; 530/345
[58] Field of Search .................... 514/18; 530/330, 345

[56] References Cited

U.S. PATENT DOCUMENTS

| | | | |
|---|---|---|---|
| 4,369,137 | 1/1983 | Hearner | 260/112.5 |
| 4,613,586 | 9/1986 | Barchas | 514/13 |
| 4,631,211 | 12/1986 | Houghten | 428/35 |

OTHER PUBLICATIONS

Pinilla, Clemencia et al., "Rapid Identification of High Affinity Peptide Ligands Using Positional Scanning Synthetic Peptide Combinatorial Libraries." Biotech. 13:901–905 (1992).
Houghten, R. A. et al., "The Use of Synthetic Peptide Combinatorial Libraries for the Identification of Bioactive Peptides." Biotech. 13:412–421 (1992).
Tam, James P. et al., "S$_N$2 Deprotection of Synthetic Peptides with a Low Concentration of HF in Dimethyl Sulfide: Evidence and Application in Peptide Synthesis." J. Am. Chem. Soc. 105:6442–6455 (1983).
Gisin, B. F. "The Monitoring of Reactions in Solid--Phase Peptide Synthesis with Picric Acid." Analytica Chimica Acta. 58:248–249 (1972).
Houghten, Richard A. et al., "Simplified Procedure for Carrying out Simultaneous Multiple Hydrogen Fluoride Cleavages of Protected Peptide Resins." J. Peptide Protein Res. 27:673–678 (1986).
Houghten, Richard A. et al., "Generation and Use of Synthetic Peptide Combinatorial Libraries for Basic Research and Drug Discovery." Nature 354:84–86 (1991).
Blondelle, Sylvie E. et al., "Hemolytic and Antimicrobial Activities of the Twenty–Four Individual Omission Analogues of Melittin." Biochem. 30:4671–4678 (1991).
Houghten, Richard A. "General Method for the Rapid Solid–Phase Synthesis of Large Numbers Of Peptides: Specificity of Antigen–Antibody Interaction at the Level of Individual Amino Acids." Proc. Natl. Acad. Sci. USA. 82:5131–5135 (1985).
Dooley, Colette T. and Houghten, Richard A. "The Use of Positional Scanning Synthetic Peptide Combinatorial Libraries for the Rapid Determination of Opioid Receptor Ligands." Life Sciences. 52:1509–1517 (1993).
Blondelle, Sylvie E. and Houghten, Richard A. "Probing the Relationships Between the Structure and Hemolytic Activity of Melittin with a Complete Set of Leucine Substitution Analogs." Peptide Research. 4(1):12–18 (1991).
Cuervo, Julio H. et al. "The Magainins: Sequence Factors Relevant to Increased Antimicrobial Activity and Decreased Hemolytic Activity." Peptide Research. 1(2):81–86 (1988).
Cuervo et al., Synthesis and antimicrobial activity of magainin alanine substitution analogs. In: "Peptides, Proceedings of the 11th American Peptide Symposium" (J. E. Rivier and G. Marshall, Eds.). Escom Science Publishers B.V., The Netherlands 1240126 (1990).
Blondelle et al., The effect of induced conformation on antimicrobial and hemolytic activity of amphipathic peptides. In: "Peptides 1990: Proceedings of the 21st (List continued on next page)

*Primary Examiner*—Jill Warden
*Assistant Examiner*—David Lukton
*Attorney, Agent, or Firm*—Campbell and Flores

[57] ABSTRACT

Peptides having Anti-microbial activity and having the formula (KFmoc)ZZZ-NH$_2$, wherein Z is an amino acid are disclosed. Also disclosed are peptides having anti-trypsin activity and having the formula Ac-rypwz-NH$_2$, wherein z is a D-amino acid. Also disclosed are compositions containing these peptides and methods of using them.

10 Claims, No Drawings

OTHER PUBLICATIONS

European Peptide Symposium" (E. Giralt and D. Andreu, Eds.) ESCOM Science Publishers B.V., 738–739 (1991).

Blondelle and Houghten, "Design of model amphipathic peptides having potent antimicrobial activities" *Biochemistry* 31:12688–12694 (1992).

Houghten et al., The use of a peptide library composed of 34, 012,224 hexamers for basic research and drug discovery. In: "Peptides: Chemistry and Biology, Proceedings of the 12th American Peptide Symposium" (J. A. Smith and J. E. Rivier, Eds.) ESCOM, Leiden 560–561 (1992).

Houghten et al., "The use of synthetic peptide combinatorial libraries for the identification of bioactive peptides" *Biotechniques* 13(3):412–421 (1992).

Houghten et al., Development of new antimicrobial agents using a synthetic peptide combinatorial library involving more than 34 million hexamers. In: "Innovation and Perspectives in Solid Phase Synthesis: Peptides, Polypeptides and Oligonucleotides" (R. Epton, Ed.) Intercept Limited, Andover, 237–239 (1992).

Blondelle et al., The relationship between potential induced conformation of melittin and its hemolytic activity. In "Peptides: Chemistry and Biology, Proceedings of the 12th American Peptide Symposium" (J. A. Smith and J. E. Rivier, Eds.) ESCOM, Leiden, 433–434 (1992).

Blondelle and Houghten, Role of individual amino acid residues on melittin's haemolytic activity. In: "Innovation and Perspectives in Solid Phase Synthesis: Peptides, Polypeptides and Oligonucleotides" (R. Epton, Ed.) Intercept Limited, Andover, 121–127 (1992).

Blondelle et al., Inhibition of melittin's hemolytic activity using synthetic peptide combinatorial libraries. In: "Peptides 1992: Proceedings of the 22nd European Peptide Symposium" (C. H. Schneider & A. N. Eberle, Eds.) ESCOM, Leiden, 761–762 (1993).

Houghten et al., "The systematic development of peptides having potent antimicrobial activity against *E. coli* through the use of synthetic peptide combinatorial libraries." *Techniques In Protein Chemistry IV,* 249–256 (1993).

Eichler and Houghten, "Preparation of synthetic peptide combinatorial libraries on cotton carriers and their application to the identification of trypsin inhibitors." *Peptides,* 320–321 (1992).

Bodansky *Principles of Peptide Synthesis,* pp. 125–126 1984.

PEPTIDES OF THE FORMULA (KFMOC) ZZZ AND THEIR USES

BACKGROUND OF THE INVENTION

This invention relates to the field of biologically active peptides and, in particular to peptides having anti-microbial activity, hemolytic activity, anti-melittin activity or anti-enzymatic activity.

Melittin, a 26-residue peptide, is the predominant compound isolated from honey bee venom (*Apis mellifera*). Melittin is known for its marked cytolytic activities, as well as for its allergenic properties. Earlier studies using individual peptide analogues of melittin (*Peptide Research* 4(1): 12–18, 1991; *Biochemistry* 30(19): 4671–4678, 1991), showed that the initial step of the mechanism of melittin's hemolytic activity involves interactions and/or binding between melittin and the lipid groups of the membrane. Compounds which would inhibit these interactions and/or bindings, would prevent the allergenic and/or lytic action of melittin in the bee venom. Furthermore, the generation of such a compound would give insight into the mechanism of action of melittin in its lytic activity.

Recent advances in technology have provided methods for the preparation and screening of a large mumber of individual peptides. Peptides identified in this manner have included peptides binding to antibody combining sites, among other things. There is a need in the art for peptides that have useful levels of anti-microbial activity, hemolytic activity, anti-melittin activity or anti-enzymatic activity. This invention satisfies these needs by providing such bio-active peptides.

SUMMARY OF THE INVENTION

This invention provides peptides having anti-microbial activity and having the formula (KFmoc)ZZZ-NH$_2$ [SEQ ID NO: 1], wherein Z is an amino acid; compositions having the aforementioned peptide in an acceptable carrier; and pharmaceutical compositions having the aforementioned peptide in a pharmaceutically acceptable carrier wherein the peptide has HD$_{50}$ greater than 100 $\mu$gms/ml. This invention also provides methods of treating a subject having a microbial infection having the step of administering to the subject a therapeutically effective amount of the aforementioned pharmaceutical composition. This invention also provides methods of inhibiting the growth of a microorganism having the step of contacting the microorganism with an effective amount of an aforementioned anti-microbial peptide. This invention also provides methods of lysing red blood cells having the step of contacting red blood cells with an effective amount of an aforementioned peptide.

This invention provides compositions having a peptide having anti-microbial activity and having the formula Ac-RRWWCZ-NH$_2$, wherein Z is an amino acid; compositions having the aforementioned peptide in an acceptable carrier; and pharmaceutical compositions having the aforementioned peptide wherein the peptide has HD$_{50}$ greater than 100 $\mu$gms/ml, in a pharmaceutically acceptable carrier. This invention also provides methods of treating a subject infected with a gram negative bacterium or yeast having the step of administering to the subject a therapeutically effective amount of the aforementioned pharmaceutical composition. This invention provides methods of inhibiting the growth of a gram negative bacteria or yeast having the step of contacting the gram negative bacteria or yeast with an effective amount of the aforementioned peptide.

This invention provides anti-microbial peptides having the formula Ac-rrwwcz-NH$_2$, wherein z is a D-amino acid; compositions having the aforementioned peptide in an acceptable carrier; and pharmaceutical compositions having the aforementioned peptide in a pharmaceutically acceptable carrier and having HD$_{50}$ greater than 100 $\mu$gms/ml. This invention also provides methods of treating a subject having a microbial infection having the step of administering to the subject a therapeutically effective amount of the aforementioned pharmaceutical composition, methods of inhibiting the growth of a microorganism having the step of contacting the microorganism with an effective amount of the aforementioned peptide; and methods of lysing red blood cells having the step of contacting red blood cells with an effective amount of the aforementioned peptide having HD$_{50}$ less than 100 $\mu$gms/ml;

This invention provides peptides having anti-melittin activity and having the formula Ac-IVILTZ-NH$_2$ [SEQ ID NO:9], Ac-IVILLZ-NH$_2$ [SEQ ID NO: 10]or Ac-IVIFFZ-NH$_2$ [SEQ ID NO: 11], wherein Z is an amino acid; and Ac-Z$_1$Z$_2$IZ$_3$Z$_4$Z$_5$-NH$_2$ [SEQ ID NO: 12], wherein Z$_1$, Z$_2$, Z$_3$, Z$_4$ and Z$_5$ are amino acids; Ac-MILWIE-NH$_2$ [SEQ ID NO:13], Ac-VIQQFV-NH$_2$ [SEQ ID NO:14] and Ac-WIQIFI-NH$_2$ [SEQ ID NO:15]; compositions having any of the aforementioned peptides in an acceptable carrier; and pharmaceutical compositions having any of the aforementioned peptides in a pharmaceutically acceptable carrier wherein the peptides has IC$_{50}$ less than 30 $\mu$gms/ml. This invention also provides methods of inhibiting melittin activity having the step of contacting melittin with an effective amount of any of the aforementioned peptides; and methods of treating a subject suffering from melittin poisoning having the step of administering to the subject a therapeutically effective amount of the aforementioned pharmaceutical composition.

This invention provides peptides having the formula Ac-ryrpwz-NH$_2$, wherein z a D-amino acid, said peptide having an IC$_{50}$ less than 150 $\mu$M against trypsin. This invention provides methods of inhibiting trypsin activity having the step of contacting trypsin with an effective amount of the aforementioned peptide.

DETAILED DESCRIPTION OF THIS INVENTION

This invention provides peptides having anti-microbial activity. These peptides inhibit the growth of microorganisms. This invention also provides peptides with high hemolytic activity. These peptides cause the lysis of red blood cells. This invention also provides peptides with anti-melittin activity. These peptides inhibit the ability of melittin to lyse red blood cells. This invention also provides peptides having anti-trypsin activity. These peptides inhibit the protolyptic action of trypsin. The disclosure of U.S. Pat. No. 4,631,211 is incorporated herein by reference.

As used herein, the term "amino acid" refers both to the naturally occurring amino acids and their derivatives, such as TyrMe and PheCl, as well as other moieties characterized by the presence of both available carboxyl group and amine group. Non-amino acid moieties which can be contained in such peptides include, for example, amino acid mimicking structures. Mimicking structures are those structures which exhibit substantially the same spatial arrangement of functional groups as amino acids but do not necessarily have both the α-amino and α-carboxyl groups characteristic of amino acids.

This invention provides generic peptides having a formula wherein "Z" designates an amino acid as defined above. According to certain embodiments of this invention, Z is an amino acid specified in Table 1; an L-amino acid; one of the twenty naturally occuring L-amino acids; a D-amino acid; or a D-amino acid version of one of the twenty naturally occuring L-amino acids.

Table 1 presents a list of amino acids referred to herein. The first column of lists abbreviations for amino acids as used in this specification. The second column lists amino acid abbreviations set forth in 37 C.F.R. §1.822. The third column lists amino acids by name.

TABLE 1

| Spec Abbreviation | 37 C.F.R § 1.822 Abbreviation | Name |
|---|---|---|
| A | Ala | L-Alanine |
| R | Arg | L-Arginine |
| N | Asn | L-Asparagine |
| D | Asp | L-Aspartic Acid |
| C | Cys | L-Cysteine |
| E | Glu | L-Glutamic Acid |
| Q | Gln | L-Glutamine |
| G, g | Gly | Glycine |
| H | His | L-Histidine |
| I | Ile | L-Isoleucine |
| L | Leu | L-Leucine |
| K | Lys | L-Lysine |
| M | Met | L-Methionine |
| F | Phe | L-Phenylalanine |
| P | Pro | L-Proline |
| S | Ser | L-Serine |
| T | Thr | L-Threonine |
| W | Trp | L-Tryptophan |
| Y | Tyr | L-Tyrosine |
| V | Val | L-Valine |
| Z, z | Xaa | Specified amino acid |
| X | | Equimolar mixture of specified amino acids |
| a | | D-Alanine |
| r | | D-Arginine |
| n | | D-Asparagine |
| d | | D-Aspartic Acid |
| c | | D-Cysteine |
| e | | D-Glutamic Acid |
| q | | D-Glutamine |
| h | | D-Histidine |
| i | | D-Isoleucine |
| l | | D-Leucine |
| k | | D-Lysine |
| m | | D-Methionine |
| f | | D-Phenylalanine |
| p | | D-Proline |
| s | | D-Serine |
| t | | D-Threonine |
| w | | D-Tryptophan |
| y | | D-Tyrosine |
| v | | D-Valine |
| Bala | bAla | beta-alanine |
| aABA | Abu | alpha-amino butyric acid |
| gABA | 4Abu | gamma-amino butyric acid |
| aAIB | Aib | alpha-amino isobutyric acid |

TABLE 1-continued

| Spec Abbreviation | 37 C.F.R § 1.822 Abbreviation | Name |
|---|---|---|
| eAca | Acp | epsilon-amino caproic acid |
| bAsp | | Beta-aspartic acid |
| gGlu | | gamma-glutamic acid |
| Cys(ACM) | | cysteine (ACM) |
| KCBZ | | epsilon-lysine |
| KFmoc | | epsilon-lysine (a-Fmoc) |
| MetO2 | | methionine sulfone |
| Nle | | norleucine |
| Nve | | norvaline |
| Orn | Orn | ornithine |
| dOrn | | delta-ornithine |
| NO2F | | p-nitro-phenylalanine |
| Hyp | 3Hyp | hydroxyproline |
| Thiopro | | thioproline |
| 7aHa | | 7-amino heptanoic acid |

As used herein, Ac- is an acetyl group of an acetylated amino-terminal amino acid of the formula:

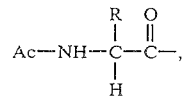

wherein R is the side chain.

As used herein, -NH2 is the amido group of an amidated, carboxy-terminal amino acid residue of the formula:

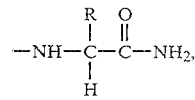

where R is the side chain.

As used herein, the term "all-D-amino acid peptide" refers to a peptide containing only D-amino acids.

I. ANTI-MICROBIAL AND HEMOLYTIC PEPTIDES

This invention provides peptides having anti-microbial activity. As used herein, the term "anti-microbial activity" means having IC50 less than 30 μgms/ml against a bacteria and IC50 less than 100 μgms/ml against a yeast. More specifically, these peptides have anti-microbial activity against bacteria such as gram-negative bacteria (e.g., *E. coli* or *P. aeruginosa*), gram-positive bacteria (e.g., *S. aureus* or *S. sanguis*) and against yeast (e.g., *C. albicans*). Several of these peptides combine high anti-microbial activity with low hemolytic activity. As used herein, the term "low hemolytic activity" means having HD50 (% hemolysis) greater than 100 μgms/ml. In one embodiment of this invention, peptides have an anti-microbial activity less than 10 gms/ml against a bacterium or yeast.

This invention also provides peptides that find use due to their high hemolytic activity, without regard to their anti-microbial activity. As used herein, the term "high hemolytic activity" means having HD50 (% hemolysis) less than 100 μgms/ml.

A. (KFmoc)ZZZ-NH₂

This invention provides anti-microbial peptides having the general formulae:

| SEQUENCE ID NO: | PEPTIDE |
| --- | --- |
| 1 | (KFmoc)ZZZ-NH₂ |
| 2 | (KFmoc)WZZ-NH₂ |
| 3 | (KFmoc)WKZ-NH₂ |
| 4 | (KFmoc)WYZ-NH₂ |
| — | (KFmoc)WfZ-NH₂ |
| — | (KFmoc)ciZ-NH₂, | wherein Z is an amino acid.

In particular, this invention provides anti-microbial peptides having the formula:

| SEQUENCE ID NO: | PEPTIDE |
| --- | --- |
| 3 | (KFmoc)WKW-NH₂ |
| 3 | (KFmoc)WKC-NH₂ |
| 3 | (KFmoc)WKF-NH₂ |
| 3 | (KFmoc)WKS-NH₂ |
| 3 | (KFmoc)WKM-NH₂ |
| 3 | (KFmoc)WKY-NH₂ |
| 3 | (KFmoc)WKK-NH₂ |
| 3 | (KFmoc)WKT-NH₂ |
| 3 | (KFmoc)WKR-NH₂ |
| 3 | (KFmoc)WKG-NH₂ |
| 3 | (KFmoc)WKZ-NH₂ |
| 3 | (KFmoc)WKL-NH₂ |
| 3 | (KFmoc)WKH-NH₂ |
| 3 | (KFmoc)WKV-NH₂ |
| 3 | (KFmoc)WKI-NH₂ |
| 3 | (KFmoc)WKN-NH₂ |
| 3 | (KFmoc)WKA-NH₂ |
| 3 | (KFmoc)WKQ-NH₂ |
| 3 | (KFmoc)WKP-NH₂ |
| 3 | (KFmoc)WKD-NH₂ |
| 3 | (KFmoc)WKE-NH₂ |
| 2 | (KFmoc)WZZ-NH₂ |
| 1 | (KFmoc)ZZZ-NH₂ |
| — | (KFmoc)WKw-NH₂ |
| — | (KFmoc)WKc-NH₂ |
| — | (KFmoc)WKl-NH₂ |
| — | (KFmoc)WKs-NH₂ |
| — | (KFmoc)WKh-NH₂ |
| — | (KFmoc)WKy-NH₂ |
| — | (KFmoc)WK(gABA)-NH₂ |
| — | (KFmoc)WKr-NH₂ |
| — | (KFmoc)WKa-NH₂ |
| — | (KFmoc)WKq-NH₂ |
| — | (KFmoc)WKm-NH₂ |
| — | (KFmoc)WKz-NH₂ |
| — | (KFmoc)WKp-NH₂ |
| — | (KFmoc)WKk-NH₂ |
| — | (KFmoc)WKi-NH₂ |
| — | (KFmoc)WKv-NH₂ |
| — | (KFmoc)WKt-NH₂ |
| — | (KFmoc)WKf-NH₂ |
| — | (KFmoc)WKn-NH₂ |
| — | (KFmoc)WKd-NH₂ |
| — | (KFmoc)WKe-NH₂ |
| 3 | (KFmoc)WK(NO₂F)-NH₂ |
| 3 | (KFmoc)WK(Orn)-NH₂ |
| 3 | (KFmoc)WK(dOrn)-NH₂ |
| 3 | (KFmoc)WK(aABA)-NH₂ |
| 3 | (KFmoc)WK(Nle)-NH₂ |
| 3 | (KFmoc)WKZ-NH₂ |
| 3 | (KFmoc)WK(KFmoc)-NH₂ |
| 3 | (KFmoc)WK(aAIB)-NH₂ |
| 3 | (KFmoc)WK(KCBZ)-NH₂ |
| 3 | (KFmoc)WK(MetO₂)-NH₂ |
| 3 | (KFmoc)WK(Hyp)-NH₂ |
| 3 | (KFmoc)WK(Nve)-NH₂ |
| 3 | (KFmoc)WK(Cys[ACM])-NH₂ |
| 3 | (KFmoc)WK(Bala)-NH₂ |
| 3 | (KFmoc)WK(Thiopro)-NH₂ |
| 3 | (KFmoc)WK(bAsp)-NH₂ |
| 3 | (KFmoc)WK(7aHa)-NH₂ |
| 3 | (KFmoc)WK(gGlu)-NH₂ |
| 3 | (KFmoc)WK(gABA)-NH₂ |
| 3 | (KFmoc)WK(eAca)-NH₂ |
| 4 | (KFmoc)WYR-NH₂ |
| 4 | (KFmoc)WYK-NH₂ |
| 4 | (KFmoc)WYL-NH₂ |
| 4 | (KFmoc)WYW-NH₂ |
| 4 | (KFmoc)WYT-NH₂ |
| 4 | (KFmoc)WYH-NH₂ |
| 4 | (KFmoc)WYY-NH₂ |
| 4 | (KFmoc)WYZ-NH₂ |
| 4 | (KFmoc)WYP-NH₂ |
| 4 | (KFmoc)WYV-NH₂ |
| 4 | (KFmoc)WYG-NH₂ |
| 4 | (KFmoc)WYA-NH₂ |
| 4 | (KFmoc)WYN-NH₂ |
| 4 | (KFmoc)WYS-NH₂ |
| 4 | (KFmoc)WYQ-NH₂ |
| 4 | (KFmoc)WYM-NH₂ |
| 4 | (KFmoc)WYI-NH₂ |
| 4 | (KFmoc)WYC-NH₂ |
| 4 | (KFmoc)WYF-NH₂ |
| 2 | (KFmoc)WZZ-NH₂ |
| 1 | (KFmoc)ZZZ-NH₂ |
| — | (KFmoc)WYr-NH₂ |
| — | (KFmoc)WYs-NH₂ |
| — | (KFmoc)WYa-NH₂ |
| — | (KFmoc)WYk-NH₂ |
| — | (KFmoc)WYp-NH₂ |
| — | (KFmoc)WYn-NH₂ |
| — | (KFmoc)WYh-NH₂ |
| — | (KFmoc)WYl-NH₂ |
| — | (KFmoc)WfK-NH₂ |
| 4 | (KFmoc)WYZ-NH₂ |
| — | (KFmoc)WYm-NH₂ |
| — | (KFmoc)WYv-NH₂ |
| — | (KFmoc)WYt-NH₂ |
| — | (KFmoc)WYq-NH₂ |
| — | (KFmoc)WYi-NH₂ |
| — | (KFmoc)WYf-NH₂ |
| — | (KFmoc)WYw-NH₂ |
| — | (KFmoc)WYc-NH₂ |
| — | (KFmoc)WYy-NH₂ |
| 4 | (KFmoc)WY(aABA)-NH₂ |
| 4 | (KFmoc)WY(7aHa)-NH₂ |
| 4 | (KFmoc)WY(dOrn)-NH₂ |
| 4 | (KFmoc)WY(Orn)-NH₂ |
| 4 | (KFmoc)WYZ-NH₂ |
| 4 | (KFmoc)WY(KCBZ)-NH₂ |
| 4 | (KFmoc)WY(Hyp)-NH₂ |
| 4 | (KFmoc)WY(aAIB)-NH₂ |
| 4 | (KFmoc)WY(Nle)-NH₂ |
| 4 | (KFmoc)WY(eAca)-NH₂ |
| 4 | (KFmoc)WY(NO₂F)-NH₂ |
| 4 | (KFmoc)WY(Bala)-NH₂ |
| 4 | (KFmoc)WY(Thiopro)-NH₂ |
| 4 | (KFmoc)WY(Nve)-NH₂ |
| 4 | (KFmoc)WY(Cys[ACM])-NH₂ |
| 4 | (KFmoc)WY(gABA)-NH₂ |
| 4 | (KFmoc)WY(MetO₂)-NH₂ |
| — | (KFmoc)WfR-NH₂ |
| — | (KFmoc)WfL-NH₂ |
| — | (KFmoc)WfP-NH₂ |
| — | (KFmoc)WfZ-NH₂ |
| — | (KFmoc)WfK-NH₂ |
| — | (KFmoc)WfN-NH₂ |
| — | (KFmoc)WfH-NH₂ |
| — | (KFmoc)WfT-NH₂ |
| — | (KFmoc)WfV-NH₂ |
| — | (KFmoc)WfS-NH₂ |
| — | (KFmoc)WfA-NH₂ |
| — | (KFmoc)WfM-NH₂ |
| — | (KFmoc)WfF-NH₂ |
| — | (KFmoc)WfC-NH₂ |
| — | (KFmoc)WfI-NH₂ |
| — | (KFmoc)WfY-NH₂ |
| 2 | (KFmoc)WZZ-NH₂ |
| 1 | (KFmoc)ZZZ-NH₂ |

| SEQUENCE ID NO: | PEPTIDE |
| --- | --- |
| — | (KFmoc)Wfl-NH$_2$ |
| — | (KFmoc)Wfw-NH$_2$ |
| — | (KFmoc)Wfr-NH$_2$ |
| — | (KFmoc)Wfi-NH$_2$ |
| — | (KFmoc)WfZ-NH$_2$ |
| — | (KFmoc)Wff-NH$_2$ |
| — | (KFmoc)Wfm-NH$_2$ |
| — | (KFmoc)Wfv-NH$_2$ |
| — | (KFmoc)Wfp-NH$_2$ |
| — | (KFmoc)Wft-NH$_2$ |
| — | (KFmoc)Wfa-NH$_2$ |
| — | (KFmoc)Wfs-NH$_2$ |
| — | (KFmoc)Wfh-NH$_2$ |
| — | (KFmoc)Wfk-NH$_2$ |
| — | (KFmoc)Wfq-NH$_2$ |
| — | (KFmoc)Wfy-NH$_2$ |
| — | (KFmoc)Wfc-NH$_2$ |
| — | (KFmoc)Wfn-NH$_2$ |
| — | (KFmoc)Wf(KCBZ)-NH$_2$ |
| — | (KFmoc)Wf(Thiopro)-NH$_2$ |
| — | (KFmoc)Wf(dOrn)-NH$_2$ |
| — | (KFmoc)Wf(Orn)-NH$_2$ |
| — | (KFmoc)Wf(aAIB)-NH$_2$ |
| — | (KFmoc)WfZ-NH$_2$ |
| — | (KFmoc)Wf(MetO$_2$)-NH$_2$ |
| — | (KFmoc)Wf(Hyp)-NH$_2$ |
| — | (KFmoc)Wf(Nve)-NH$_2$ |
| — | (KFmoc)Wf(aABA)-NH$_2$ |
| — | (KFmoc)Wf(7aHa)-NH$_2$ |
| — | (KFmoc)Wf(Nle)-NH$_2$ |
| — | (KFmoc)Wf(No$_2$F)-NH$_2$ |
| — | (KFmoc)Wf(gABA)-NH$_2$ |
| — | (KFmoc)Wf(Bala)-NH$_2$ |
| — | (KFmoc)Wf(Cys[ACM])-NH$_2$ |
| — | (KFmoc)ciR-NH$_2$ |
| — | (KFmoc)ciK-NH$_2$ |
| — | (KFmoc)ciP-NH$_2$ |
| — | (KFmoc)ciM-NH$_2$ |
| — | (KFmoc)ciH-NH$_2$ |
| — | (KFmoc)ciA-NH$_2$ |
| — | (KFmoc)ciW-NH$_2$ |
| — | (KFmoc)ciT-NH$_2$ |
| — | (KFmoc)ciL-NH$_2$ |
| — | (KFmoc)ciZ-NH$_2$ |
| — | (KFmoc)ciY-NH$_2$ |
| — | (KFmoc)ciS-NH$_2$ |
| — | (KFmoc)ciI-NH$_2$ |
| — | (KFmoc)ciF-NH$_2$ |
| — | (KFmoc)ciN-NH$_2$ |
| — | (KFmoc)ciV-NH$_2$ |
| — | (KFmoc)cZZ-NH$_2$ |
| 1 | (KFmoc)ZZZ-NH$_2$ |
| — | (KFmoc)cir-NH$_2$ |
| — | (KFmoc)cik-NH$_2$ |
| — | (KFmoc)cip-NH$_2$ |
| — | (KFmoc)cil-NH$_2$ |
| — | (KFmoc)ciZ-NH$_2$ |
| — | (KFmoc)cit-NH$_2$ |
| — | (KFmoc)ciw-NH$_2$ |
| — | (KFmoc)cim-NH$_2$ |
| — | (KFmoc)cic-NH$_2$ |
| — | (KFmoc)cif-NH$_2$ |
| — | (KFmoc)ciy-NH$_2$ |
| — | (KFmoc)cis-NH$_2$ |
| — | (KFmoc)ci(aAIB)-NH$_2$ |
| — | (KFmoc)ci(Orn)-NH$_2$ |
| — | (KFmoc)ci(dOrn)-NH$_2$ |
| — | (KFmoc)ci(KCBZ)-NH$_2$ |
| — | (KFmoc)ci(aABA)-NH$_2$ |
| — | (KFmoc)ci(Hyp)-NH$_2$ |
| — | (KFmoc)ci(Thiopro)-NH$_2$ |
| — | (KFmoc)ciZ-NH$_2$ |
| — | (KFmoc)ci(KFmoc)-NH$_2$ |
| — | (KFmoc)ci(7aHa)-NH$_2$ |
| — | (KFmoc)ci(eAca)-NH$_2$ |
| — | (KFmoc)ci(Nve)-NH$_2$ |
| — | (KFmoc)ci(Nle)-NH$_2$ |
| — | (KFmoc)ci(NO$_2$F)-NH$_2$ |

In particular, this invention provides anti-microbial peptides having the formula (KFmoc)ZZZ-NH$_2$[SEQ ID NO:1], wherein Z is an amico acid said peptide having an IC$_{50}$ less than 30 μgms/ml and more particularly, HD$_{50}$ (% hemolysis) greater than 100 μgms/ml.

This invention provides compositions comprising anti-microbial or hemolytic peptides, in particular having the formula (KFmoc)ZZZ-NH$_2$[SEQ ID NO:1], wherein Z is an amino acid, in an acceptable carrier. These compositions find use as disinfectants and in methods to retard the growth of microorganisms. They also find use in methods of treating subjects with microbial infections. Compositions comprising hemolytic peptides find use, e.g., in diagnostic procedures requiring lysis of red blood cells.

This invention provides pharmaceutical compositions comprising a peptide having the formula (KFmoc)ZZZ-NH$_2$, wherein Z is an amino acid in a pharmaceutically acceptable carrier, said peptide having anti-microbial activity. In particular, this invention provides pharmaceutical compositions in which the peptide has HD$_{50}$ greater than 100 μgms/ml.

This invention provides methods of treating a subject infected with a microorganism comprising the step of administering to the subject a therapeutically effective amount of a pharmaceutical composition comprising a peptide having the formula (KFmoc)ZZZ-NH$_2$[SEQ ID NO:1], wherein Z is an amino acid, said peptide having anti-microbial activity against the said microorganism. In particular, this invention provides methods in which the peptide has HD$_{50}$ greater than 100 μgms/ml.

This invention provides methods of inhibiting the growth of a microorganism comprising the step of contacting the microorganism with an effective amount of a peptide having the formula (KFmoc)ZZZ-NH$_2$[SEQ ID NO:1], wherein Z is an amino acid, said peptide having anti-microbial activity against the microorganism. In particular, this invention provides this method wherein the peptide has HD$_{50}$ greater than 100 μgms/ml. An effective amount is at least the IC$_{50}$ concentration.

This invention also provides methods of lysing red blood cells comprising the step of contacting red blood cells with an effective amount of a peptide having the formula (KFmoc)ZZZ-NH$_2$[SEQ ID NO:1], wherein Z is an amino acid, and the peptide has HD$_{50}$ less than 100 μgms/ml. An effective amount is at least the IC$_{50}$ concentration.

B. Ac-RRWWCZ-NH$_2$ [SEQ ID NO:6]

This invention provides methods using anti-microbial peptides having the general formulae:

| SEQUENCE ID NO: | PEPTIDE |
| --- | --- |
| 5 | Ac-RRWWZZ-NH$_2$ |
| 6 | Ac-RRWWCZ-NH$_2$ | wherein Z is an amino acid.

In particular, this invention provides methods using peptides having the formula:

| SEQUENCE ID NO: | PEPTIDE |
| --- | --- |
| 6 | Ac-RRWWCA-NH$_2$ |
| 6 | Ac-RRWWCC-NH$_2$ |
| 6 | Ac-RRWWCD-NH$_2$ |
| 6 | Ac-RRWWCE-NH$_2$ |
| 6 | Ac-RRWWCF-NH$_2$ |

-continued

| SEQUENCE ID NO: | PEPTIDE |
| --- | --- |
| 6 | Ac-RRWWCG-NH$_2$ |
| 6 | Ac-RRWWCH-NH$_2$ |
| 6 | Ac-RRWWCI-NH$_2$ |
| 6 | Ac-RRWWCK-NH$_2$ |
| 6 | Ac-RRWWCL-NH$_2$ |
| 6 | Ac-RRWWCM-NH$_2$ |
| 6 | Ac-RRWWCN-NH$_2$ |
| 6 | Ac-RRWWCP-NH$_2$ |
| 6 | Ac-RRWWCQ-NH$_2$ |
| 6 | Ac-RRWWCR-NH$_2$ |
| 6 | Ac-RRWWCS-NH$_2$ |
| 6 | Ac-RRWWCT-NH$_2$ |
| 6 | Ac-RRWWCV-NH$_2$ |
| 6 | Ac-RRWWCW-NH$_2$ |
| 6 | Ac-RRWWCY-NH$_2$ |

This invention also provides pharmaceutical compositions comprising a peptide having the formula Ac-RRWWCZ-NH$_2$[SEQ ID NO: 6], wherein Z is an amino acid, in a pharmaceutically acceptable carrier, said peptide having an IC$_{50}$ less than 30 μgms/ml against E. coli, S. aureus, S. sangiunis, C. albicans or P. aeruginosa. In particular, this invention provides pharmaceutical compositions in which the peptide has HD$_{50}$ greater than 100 μgms/ml.

This invention also provides methods of treating a subject infected with a gram-negative bacterium (e.g. E. coli or P. aeruginosa), or a yeast (e.g. C. albicans) comprising the step of administering to the subject a therapeutically effective amount of a pharmaceutical composition comprising a peptide having the formula Ac-RRWWCZ-NH$_2$, [SEQ ID NO:6] or Ac-rrwwcz-NH$_2$, wherein z is a D-amino acid, in a pharmaceutically acceptable carrier, said peptide having an IC$_{50}$ less than 30 μgms/ml against the microorganism. In particular, this invention provides methods in which the peptide has HD$_{50}$ greater than 100 μgms/ml.

This invention also provides methods of inhibiting the growth of a gram-negative bacterium (e.g. E. coli or P. aeruginosa), or a yeast (e.g., C. albicans) comprising the step of contacting the microorganism with an effective amount of a peptide having the formula Ac-RRWWCZ-NH$_2$, wherein Z is an amino acid, said peptide having an IC$_{50}$ less than 30 μgms/ml against the microorganism. In particular, this invention provide methods wherein the peptide has HD$_{50}$ greater than 100 μgms/ml. An effective amount is at least the IC$_{50}$ concentration.

This invention also provides methods of lysing red blood cells comprising the step of contacting red blood cells with an effective amount of a peptide having the formula Ac-RRWWCZ-NH$_2$, [SEQ. ID NO:6] wherein Z is an amino acid, wherein the peptide has HD$_{50}$ less than 100 μgms/ml. An effective amount is at least the IC$_{50}$ concentration.

C. Ac -rrwwz -NH$_2$

This invention also provides anti-microbial peptides having the formula:

| SEQUENCE ID NO: | PEPTIDE |
| --- | --- |
| — | Ac-rrwwz-NH$_2$, | wherein Z is an amino acid, and, in particular, wherein z is a D-amino acid; wherein the peptide has anti-microbial activity IC$_{50}$ less than 30 μgms/ml and more particularly, less than 10 μgms/ml. It also provides these peptides having HD$_{50}$ greater than 100 μgms/ml.

In particular, this invention provides peptides having the formula:

| SEQUENCE ID NO: | PEPTIDE |
| --- | --- |
| — | Ac-rrwwcr-NH$_2$ |
| — | Ac-rrwwcv-NH$_2$ |

This invention provides pharmaceutical compositions comprising a peptide having the formula (KFmoc)ZZZ-NH$_2$, wherein Z is an amino acid in a pharmaceutically acceptable carrier, said peptide having anti-microbial activity. In particular, this invention provides pharmaceutical compositions in which the peptide has HD$_{50}$ greater than 100 μgms/ml.

This invention provides methods of treating a subject infected with a microorganism comprising the step of administering to the subject a therapeutically effective amount of a pharmaceutical composition comprising a peptide having the formula wherein z is a D-amino acid said peptide having anti-microbial activity against the said microorganism. In particular, this invention provides methods in which the peptide has HD$_{50}$ greater than 100 μgms/ml.

This invention provides methods of inhibiting the growth of a microorganism comprising the step of contacting the microorganism with an effective amount of a peptide having the formula wherein z is a D-amino acid said peptide having anti-microbial activity against the microorganism. In particular, this invention provides this method wherein the peptide has HD$_{50}$ greater than 100 μgms/ml. An effective amount is at least the IC$_{50}$ concentration.

This invention also provides methods of lysing red blood cells comprising the step of contacting red blood cells with an effective amount of a peptide having the formula wherein z is a D-amino acid and the peptide has HD$_{50}$ less than 100 μgms/ml. An effective amount is at least the IC$_{50}$ concentration.

II. ANTI-MELITTIN PEPTIDES

This invention provides peptides having anti-melittin activity. Melittin is the active compound in bee venom, and causes cell lysis. It has the formula:

| SEQ ID NO: | PEPTIDE |
| --- | --- |
| 7 | GIGAVLKVLT TGLPALISW IKRKRQQ-NH$_2$ |

One can synthesize melittin by any known method for peptide synthesis.

This invention provides peptides having anti-melittin activity having the general formulae:

| SEQ ID NO: | PEPTIDE |
| --- | --- |
| 8 | Ac-IVILZZ-NH$_2$ |
| 9 | Ac-IVILTZ-NH$_2$ |
| 10 | Ac-IVILLZ-NH$_2$ |
| 11 | Ac-IVIFFZ-NH$_2$ | wherein Z is an amino acid.

In particular, this invention provides peptides having the formula:

| SEQ ID NO: | PEPTIDE |
|---|---|
| 9 | Ac-IVILTM-NH$_2$ |
| 9 | Ac-IVILTF-NH$_2$ |
| 9 | Ac-IVILTL-NH$_2$ |
| 9 | Ac-IVILTQ-NH$_2$ |
| 9 | Ac-IVILTW-NH$_2$ |
| 9 | Ac-IVILTA-NH$_2$ |
| 9 | Ac-IVILTN-NH$_2$ |
| 9 | Ac-IVILTY-NH$_2$ |
| 9 | Ac-IVILTC-NH$_2$ |
| 9 | Ac-IVILTV-NH$_2$ |
| 9 | Ac-IVILTG-NH$_2$ |
| 9 | Ac-IVILTE-NH$_2$ |
| 9 | Ac-IVILTS-NH$_2$ |
| 9 | Ac-IVILTT-NH$_2$ |
| 9 | Ac-IVILTP-NH$_2$ |
| 9 | Ac-IVILTH-NH$_2$ |
| 9 | Ac-IVILTI-NH$_2$ |
| 9 | Ac-IVILTK-NH$_2$ |
| 9 | Ac-IVILTR-NH$_2$ |
| 10 | Ac-IVILLW-NH$_2$ |
| 10 | Ac-IVILLE-NH$_2$ |
| 10 | Ac-IVILLQ-NH$_2$ |
| 10 | Ac-IVILLY-NH$_2$ |
| 10 | Ac-IVILLN-NH$_2$ |
| 10 | Ac-IVILLS-NH$_2$ |
| 10 | Ac-IVILLA-NH$_2$ |
| 10 | Ac-IVILLG-NH$_2$ |
| 10 | Ac-IVILLD-NH$_2$ |
| 10 | Ac-IVILLT-NH$_2$ |
| 10 | Ac-IVILLM-NH$_2$ |
| 10 | Ac-IVILLF-NH$_2$ |
| 10 | Ac-IVILLP-NH$_2$ |
| 10 | Ac-IVILLI-NH$_2$ |
| 10 | Ac-IVILLV-NH$_2$ |
| 10 | Ac-IVILLL-NH$_2$ |
| 10 | Ac-IVILLC-NH$_2$ |
| 10 | Ac-IVILLH-NH$_2$ |
| 10 | Ac-IVILLK-NH$_2$ |
| 10 | Ac-IVILLR-NH$_2$ |
| 11 | Ac-IVIFFD-NH$_2$ |
| 11 | Ac-IVIFFE-NH$_2$ |
| 11 | Ac-IVIFFW-NH$_2$ |
| 11 | Ac-IVIFFN-NH$_2$ |
| 11 | Ac-IVIFFM-NH$_2$ |
| 11 | Ac-IVIFFY-NH$_2$ |
| 11 | Ac-IVIFFS-NH$_2$ |
| 11 | Ac-IVIFFG-NH$_2$ |
| 11 | Ac-IVIFFT-NH$_2$ |
| 11 | Ac-IVIFFA-NH$_2$ |
| 11 | Ac-IVIFFQ-NH$_2$ |
| 11 | Ac-IVIFFV-NH$_2$ |
| 11 | Ac-IVIFFH-NH$_2$ |
| 11 | Ac-IVIFFP-NH$_2$ |
| 11 | Ac-IVIFFC-NH$_2$ |
| 11 | Ac-IVIFFI-NH$_2$ |
| 11 | Ac-IVIFFL-NH$_2$ |
| 11 | Ac-IVIFFF-NH$_2$ |
| 11 | Ac-IVIFFK-NH$_2$ |
| 11 | Ac-IVIFFR-NH$_2$ |

This invention provides peptides having anti-melittin activity having the formula:

| SEQ ID NO: | PEPTIDE |
|---|---|
| 12 | Ac-Z$_1$Z$_2$IZ$_3$Z$_4$Z$_5$-NH$_2$, | wherein Z$_1$, Z$_2$, Z$_3$, Z$_4$ and Z$_5$ are amino acids, and in particular wherein Z$_1$ is F or I; Z$_2$ is I, Q or D; Z$_3$ is W or Y; Z$_4$ is C or F and Z$_5$ is E or K.

In particular, this invention is directed to peptides having the formula:

| SEQ ID NO: | PEPTIDE |
|---|---|
| 12 | Ac-FIIWCE-NH$_2$ |
| 12 | Ac-IIIWCE-NH$_2$ |
| 12 | Ac-FIIYCE-NH$_2$ |
| 12 | Ac-IQIYCE-NH$_2$ |
| 12 | Ac-IIIYFE-NH$_2$ |
| 12 | Ac-IIIWFE-NH$_2$ |
| 12 | Ac-FIIWFE-NH$_2$ |
| 12 | Ac-IQIWCE-NH$_2$ |
| 12 | Ac-FIIYFE-NH$_2$ |
| 12 | Ac-FQIWFE-NH$_2$ |
| 12 | Ac-FQIWCE-NH$_2$ |
| 12 | Ac-IIIYCE-NH$_2$ |
| 12 | Ac-FQIYCE-NH$_2$ |
| 12 | Ac-IQIYFE-NH$_2$ |
| 12 | Ac-FQIYFE-NH$_2$ |
| 12 | Ac-IQIWFE-NH$_2$ |
| 12 | Ac-IDIWCK-NH$_2$ |
| 12 | Ac-FDIWFK-NH$_2$ |
| 12 | Ac-FDIWFE-NH$_2$ |
| 12 | Ac-FDIYCE-NH$_2$ |
| 12 | Ac-IDIYCE-NH$_2$ |
| 12 | Ac-IDIYFE-NH$_2$ |
| 12 | Ac-FIIYFK-NH$_2$ |
| 12 | Ac-IDIYFK-NH$_2$ |
| 12 | Ac-IDIWCE-NH$_2$ |
| 12 | Ac-FDIYFE-NH$_2$ |
| 12 | Ac-IQIYCK-NH$_2$ |
| 12 | Ac-FIIWFK-NH$_2$. |

This invention also provides peptides having the formula:

| SEQ ID NO: | PEPTIDE |
|---|---|
| 13 | Ac-MILWIE-NH$_2$ |
| 14 | Ac-VIQQFV-NH$_2$ |
| 15 | Ac-WIQIFI-NH$_2$ |

In particular, this invention also provides anti-melittin peptides having IC$_{50}$ less than 30 μgms/ml.

This invention provides methods of inhibiting melittin activity comprising the step of contacting melittin with an effective amount of a peptide having the formula Ac-IVILTZ-NH$_2$ [SEQ ID NO:9], Ac-IVILLZ-NH$_2$ [SEQ ID NO:10], Ac-IVIFFZ-NH$_2$ [SEQ ID NO:11], having an IC$_{50}$ less than 30 μgms/ml. An effective amount is at least the IC$_{50}$ concentration.

This invention also provides compositions comprising a peptide having the formula Ac-IVILTZ-NH$_2$ [SEQ ID NO:9], Ac-IVILLZ-NH$_2$ [SEQ ID NO:10], Ac-IVIFFZ-NH$_2$ SEQ ID NO:11], or Ac-Z$_1$ Z$_2$ IZ$_3$ Z$_4$ Z$_5$-NH$_2$, wherein Z is an amino acid, Ac-MILWIE-NH$_2$, Ac-VIQQFV-NH$_2$, Ac-WIQIFI-NH$_2$ in an acceptable carrier.

This invention also provides pharmaceutical compositions comprising a peptide having the formula Ac-IVILTZ-NH$_2$ [SEQ ID NO:9], Ac-IVILLZ-NH$_2$ [SEQ ID NO:10], Ac-IVIFFZ-NH$_2$ [SEQ ID NO:11], or Ac-Z$_1$ Z$_2$ IZ$_3$ Z$_4$ Z$_5$-NH$_2$, [SEQ ID NO:12] wherein Z is an L-amino acid, Ac-MILWIE-NH$_2$, Ac-VIQQFV-NH$_2$, Ac-WIQIFI-NH$_2$ in a pharmaceutically acceptable carrier.

This invention also provides methods of treating a subject suffering from melittin poisoning comprising the step of administering to the subject a therapeutically effective amount of a pharmaceutical composition comprising a peptide of having the formula Ac-IVILTZ-NH$_2$ [SEQ ID NO:9], Ac-IVILLZ-NH$_2$ [SEQ ID NO: 10 , Ac-IVIFFZ-NH$_2$ [SEQ ID NO:11], or Ac-Z$_1$ Z$_2$ IZ$_3$ Z4 Z$_5$, [SEQ ID NO:12] wherein Z is an L-amino acid, said peptide having an HD$_{50}$ greater than 100

μgms/ml. Melittin poisoning results from introducion of melittin into a subject to cause significant cell lysis, for example by bee sting.

III. ANTI-TRYPSIN PEPTIDES

This invention provides all-D-amino acid anti-trypsin peptides having an $IC_{50}$ less than 150 $\mu M$ at a trypsin concentration of 193 nM. These peptides find use in methods of inhibiting trypsin activity. For example, these peptides find use in quenching trypsin activity in assays or procedures calling for limited trypsin digestion.

In particular, this invention provides peptides having the formula:

| SEQ ID NO: | PEPTIDE |
|---|---|
|  | Ac-ryrpwz-NH$_2$ | wherein z is a D-amino acid.

More particularly, this invention provides the peptides:

| SEQ ID NO: | PEPTIDE |
|---|---|
| — | Ac-ryrpwp-NH$_2$ |
| — | Ac-ryrpww-NH$_2$ |
| — | Ac-ryrpwv-NH$_2$ |
| — | Ac-ryrpwc-NH$_2$ |
| — | Ac-ryrpwt-NH$_2$ |

This invention also provides methods of inhibiting trypsin activity comprising the step of contacting trypsin with an effective amount of a peptide having the formula Ac-ryrpwz-NH$_2$, wherin z is a D-amino acid. An effective amount is at least the $IC_{50}$ concentration.

One skilled in the art can easily produce any of the individual peptides of this invention by simultaneous multi peptide synthesis (Example I) or by synthesis on an automated peptide synthesizer, according to the manufacturer's instructions (Model 430A, Applied Biosystems, Foster City, Calif. USA).

This invention provides pharmaceutical compositions comprising the peptides of this invention in a pharmaceutically acceptable carrier. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents.

Suitable pharmaceutical carriers and their formulations are described in Martin, REMINGTON'S PHARMACEUTICAL SCIENCES, 15th Ed. (Mack Publishing Co., Easton 1975). Such compositions will, in general, contain an effective amount of the active reagent together with a suitable amount of carrier so as to prepare the proper dosage form for proper administration to the subject.

Useful pharmaceutical carriers for the preparation of the pharmaceutical compositions can be solids, liquids or gases. Thus, the compositions can take the form of tablets, pills, capsules, powders, enterically coated or other protected formulations (such as by binding on ion exchange resins or other carriers, or packaging in lipid protein vesicles or adding additional terminal amino acids), sustained release formulations, solutions (e.g. ophthalmic drops), suspensions, elixirs, aerosols, and the like. Water, saline, aqueous dextrose, and glycols are preferred liquid carriers, particularly (when isotonic) for injectable solutions. The carrier can be selected from various oils including those of petroleum, animal, vegetable or synthetic origin, for example, peanut oil, soybean oil, mineral oil, sesame oil, and the like. Suitable pharmaceutical excipients include starch, cellulose. talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like.

The compositions may be subjected to conventional pharmaceutical procedures such as sterilization and may contain conventional pharmaceutical additives such as preservatives, stabilizing agents, wetting or emulsifying agents, salts for adjusting osmotic pressure, buffers, and the like.

This invention provides methods of treating a subject comprising the step of administering a therapeutically effective amount of a pharmaceutical composition of this invention to a subject. As used herein, the term "therapeutically effective amount" is that amount necessary to alleviate the condition from which the subject suffers. As used herein, the term "subject" includes animals, vertebrates, mammals or humans.

In the practice of the therapeutic methods of the present invention, an effective amount of a peptide of this invention, including derivatives or salts thereof, or a pharmaceutical composition containing the same, as described above, is administered via any of the usual and acceptable methods known in the art, either singly or in combination with another peptide or peptides of the present invention or other pharmaceutical agents such as anti-inflammatory agents, or other therapeutics known to have an effect on inflammation or the like. These compounds or compositions can thus be administered orally, sublingually, topically (e.g., on the skin or in the eyes), parenterally (e.g., intramuscularly, intravenously, subcutaneously or intradermally), or by inhalation, and in the form of either solid, liquid or gaseous dosage including tablets, suspensions, and aerosols, as is discussed in more detail above. The administration can be conducted in single unit dosage form with continuous therapy or in single dose therapy ad libitum.

In one embodiment, the therapeutic methods of the present invention are practiced when the relief of symptoms is specifically required or perhaps imminently so. In another embodiment, the method is effectively practiced as continuous or prophylactic treatment.

In the practice of the therapeutic methods of the invention, the particular dosage of pharmaceutical composition to be administered to the subject will depend on a variety of considerations including the nature of the disease, the severity thereof, the schedule of administration, the age and physical characteristics of the subject, and so forth. Proper dosages may be established using clinical approaches familiar to the medicinal arts. It is presently believed that dosages in the range 0.1 of 100 mg of a peptide of this invention per kilogram of subject body weight will be useful, and a range of 1 to 100 mg per kg generally preferred where the administration is by injection or ingestion. Topical dosages may utilize formulations containing active peptides and a liquid carrier or excipient, with multiple daily applications being appropriate.

This invention also provides methods of inhibiting the growth of microorganisms comprising the step of contacting the microorganism with an effective amount of a peptide of this invention. Methods of contacting a microorganism with a peptide of this invention include, for example, those described in Example I, Section B.

This invention provides methods of inhibiting melittin activity comprising the step of contacting melittin with an effective amount of a peptide of this invention. Such methods include, for example, those described in Example II, Section B.

This invention provides methods of inhibiting trypsin activity comprising the step of contacting trypsin with an effective amount of a peptide of this invention. Such methods include, for example, those described in Example III, Section B.

EXAMPLE I

PEPTIDES HAVING ANTI-MICROBIAL ACTIVITY

A. Synthetic Peptide Libraries

A synthetic peptide library was prepared using methylbenzhydrylamine (MBHA) polystyrene resin and standard t-Boc chemistry in combination with simultaneous multiple peptide synthesis (SMPS) (R. A. Houghten, *Proc. Natl. Acad. Sci. U.S.A.* 82., 5131–5135 (1985); U.S. Pat. No. 4,631,211 (each of which is incorporated herein by reference)). A divide, couple and recombine (DCR) process was used to synthesize the XXXX-peptide resin wherein X is an equimolar mixture of selected amino acids. This process assures equimolarity of the peptides on the resin.

Briefly, 18 porous polypropylene packets, each containing 4.65 mmol (5.00 g) of MBHA resin, were coupled to each of the protected N-α-t-Boc amino acids of interest. All coupling reactions proceeded to completion (greater than 99.5%), as assessed by Gisin's picric acid (B. F. Gisin, *Analytica Chim. Acta.* 58, 248–249 (1972)) or Kaiser"s ninhydrin tests (E. T. Kaiser, *Analyt. Biochem* 34, 595–598 (1970)).

The resulting resins from each packet were then combined and thoroughly mixed. This resin mixture was separated into 18 portions of equal weight which were placed into porous polypropylene packets, followed by N-α-t-Boc protecting group removal and neutralization of the resulting amine TFA salts. The resin packets were then reacted with solutions of the individual activated amino acids to yield the 324 dipeptide combinations (18$^2$).

The above DCR process was repeated twice more, yielding a final mixture of 104,976 protected tetra-peptide resins (18$^4$). This XXXX-resin was divided into 324 aliquots (150 mg each) and placed in numbered, porous polypropylene packets.

Synthesis of the next two defined positions was carried out by SMPS. The peptide mixtures were deprotected and cleaved from their respective resins using low-high hydrogen fluoride (HF) (J. P. Tam et al., *J. Am. Chem. Soc.* 105, 6442–6455 (1983)) as described for individual peptides earlier (J. H. Cuervo et al., *Peptide Res.* 1, 81–86 (1988); and R. A. Houghten et al., *Int. J. Peptide Protein Res.* 27, 673–678 (1986)) in a multiple HF cleavage apparatus (Multiple Peptide Systems, San Diego, Calif.). Extraction of the individual peptide mixtures was carried out with distilled water.

B. Antimicrobial Assays

1. *E. coli, P. aeruginosa* and *S. aureus*

Escherichia coli ATCC 25922 and *P. aeruginosa* ATCC 27853 were used as Gram-negative (−) and *Staphylococcus aureus* ATCC 29213 as Gram-positive (+) bacteria. Bacteria were grown overnight at 37° C. in Mueller-Hinton (MH) broth. This culture was reinoculated and incubated at 37° C. to reach the exponential phase of bacteria growth, i.e., a final bacterial suspension containing $10^5$ to $5\times10^5$ colony-forming units (CFU)/ml. The concentration of cells was established by plating 100 μl of different dilutions of the culture solution (e.g., $10^{-2}$, $10^{-3}$ and $10^{-4}$) onto solid agar plates.

Following an overnight incubation at 37° C., the CFU thus formed were counted on each agar plate. In 96-well tissue culture plates, as control blanks, eight wells per plate contained only medium, while as a positive growth control, eight other wells contained medium plus cells. These controls were used to detect possible medium contamination and to provide a measure of uninhibited growth of the microorganisms.

For IC$_{50}$ (concentration necessary to inhibit 50% growth of bacteria), peptides were added to the bacterial suspension at concentrations derived from two-fold dilutions ranging from 1000 μg/ml to 1.95 μg/ml.

The plates were incubated overnight at 37° C., and the optical density (OD) determined at 620 nm after different times of incubation.

2. *S. sanguis*

Streptococcus sanguis ATCC 10556 (Gram-positive (+) bacteria present in tooth crevices) was grown overnight at 37° C. in Brain Heart Infusion (BHI) broth. This culture was reinoculated and incubated at 37° C. to reach the exponential phase of bacteria growth, i.e., a final bacterial suspension containing $10^5$ to $5\times10^5$ colony-forming units (CFU)/ml. The concentration of cells was established by plating 100 μl of different dilutions of the culture solution (e.g., $10^{-2}$, $10^{-4}$ and $10^{-4}$) onto solid agar plates. Following an overnight incubation at 37° C., the CFU thus formed were counted on each agar plate. In 96-well tissue culture plates, as control blanks, eight wells per plate contained only medium, while as a positive growth control, eight other wells contained medium plus cells. These controls were used to detect possible medium contamination and to provide a measure of uninhibited growth of the microorganisms. For IC$_{50}$ (concentration necessary to inhibit 50% growth of bacteria), peptides are added to the bacterial suspension at concentrations derived from two-fold dilutions ranging from 1000 μg/ml to 1.95 μg/ml. The plates were incubated overnight at 37° C., and the optical density (OD) determined at 620 nm after 20 to 24 hours incubation.

3. *C. albicans*

The organism used for antifungal studies was *Candida albicans* ATCC 10231. The yeast culture was spread onto YM agar plates and incubated at 30° C. for 48 hours. Three colonies of this culture (approx. 1 mm in diameter each) were then inoculated in 5 ml of 1X PBS solution. The suspension was vortexed and diluted 10-fold in YM broth, for an approximate final concentration of $10^5$ to $5\times10^5$ CFU (colony forming units)/ml. Actual concentration of yeast culture was determined by plating 100 μl of different solutions of the culture solution ($10^{-3}$, $10^{-4}$, $10^{-5}$) onto solid YM agar plates.

After 48 hours of incubation at 30° C., CFU formed were counted from each plate. The assays were carried out in 96-well tissue culture plates. Eight wells containing only medium of YM broth served as negative controls while eight wells containing medium and yeast culture served as positive controls. These controls were used to detect possible medium contamination and to provide a measure of uninhibited growth of the yeast. The two antifungal drugs Amphotericin B and Nystatin (both from Sigma Chemical, St. Louis, Mo., U.S.A.) were included in each assay for comparative purpose.

For $IC_{50}$ (concentration necessary to inhibit 50% growth of the yeast) peptides were added to the yeast suspension at concentrations derived from two-fold dilutions ranging from 1500 μg/ml to 3.13 μg/ml. The plates were incubated over a period of 48 hours at 30° C., and the optical density (OD) at 24 and 48 hours was determined at 620 nm.

C. Hemolytic Activity

Each assay was carried out in 96-well culture tissue plates. Four wells per plate contain 125 μl of a non-peptide positive control (1% Triton in de-ionized water), and four wells per plate contain 125 μl of a control blank, phosphate buffered saline (PBS). The hemolytic peptide melittin was used as comparative control. The controls served to detect possible contamination and to calculate the percent hemolysis of each peptide. Human red blood cells (RBCs) were washed with PBS and centrifuged to separate them from the serum. The cells were then resuspended in PBS to a final suspension of 0.5% RBC. 125 μl of this suspension was added to the peptides and controls solution. The release of hemoglobin resulting from the cell lysis was determined by measuring the OD at 414 nm of 100 μl of the supernatant.

The hemolytic doses, i.e., the concentration necessary to lyse 50% of the cells ($HD_{50}$), were determined by performing a serial two-fold dilution of the peptide mixture solutions ranging from 1500 μg/ml to 3.13 μg/ml.

D. Results

Tables 2–23 present data on the anti-microbial and hemolytic activities of various peptides. In Tables 2–21 "X" represents and equimolar mixture of the amino acids of Table I, excluding D- and L- cysteine and D- and L- tryptophan.

TABLE 2

ANTIMICROBIAL ACTIVITY AGAINST *E. COLI* OF (KFmoc)WKZ-NH$_2$

| | $IC_{50}$ (μg/ml) | | $IC_{50}$ (μg/ml) |
|---|---|---|---|
| (KFmoc)WKW-NH$_2$ | 14 | (KFmoc)WKw-NH$_2$ | 15 |
| (KFmoc)WKL-NH$_2$ | 18 | (KFmoc)WKl-NH$_2$ | 20 |
| (KFmoc)WKF-NH$_2$ | 20 | (KFmoc)WKc-NH$_2$ | 23 |
| (KFmoc)WKM-NH$_2$ | 26 | (KFmoc)WKi-NH$_2$ | 23 |
| (KFmoc)WKY-NH$_2$ | 27 | (KFmoc)WKf-NH$_2$ | 38 |
| (KFmoc)WKC-NH$_2$ | 28 | (KFmoc)WKy-NH$_2$ | 39 |
| (KFmoc)WKI-NH$_2$ | 29 | (KFmoc)WKp-NH$_2$ | 39 |
| (KFmoc)WKV-NH$_2$ | 32 | (KFmoc)WKm-NH$_2$ | 41 |
| (KFmoc)WKX-NH$_2$ | 41 | (KFmoc)WKX-NH$_2$ | 41 |
| (KFmoc)WKT-NH$_2$ | 42 | (KFmoc)WKn-NH$_2$ | 47 |
| (KFmoc)WKS-NH$_2$ | 46 | (KFmoc)WKh-NH$_2$ | 52 |
| (KFmoc)WKA-NH$_2$ | 50 | (KFmoc)WKv-NH$_2$ | 54 |
| (KFmoc)WKG-NH$_2$ | 66 | (KFmoc)WKt-NH$_2$ | 55 |

TABLE 2-continued

ANTIMICROBIAL ACTIVITY AGAINST *E. COLI* OF (KFmoc)WKZ-NH$_2$

| (KFmoc)WKP-NH$_2$ | 67 | (KFmoc)WKs-NH$_2$ | 57 |
|---|---|---|---|
| (KFmoc)WKR-NH$_2$ | 74 | (KFmoc)WKq-NH$_2$ | 57 |
| (KFmoc)WKQ-NH$_2$ | 75 | (KFmoc)WKa-NH$_2$ | 60 |
| (KFmoc)WXX-NH$_2$ | 32 | (KFmoc)WKr-NH$_2$ | 66 |
| (KFmoc)ZXX-NH$_2$ | 179 | | |

| | $IC_{50}$ (μg/ml) |
|---|---|
| (KFmoc)WK(NO$_2$F)-NH$_2$ | 18 |
| (KFmoc)WK(Nle)-NH$_2$ | 26 |
| (KFmoc)WK(Nve)-NH$_2$ | 32 |
| (KFmoc)WKX-NH$_2$ | 41 |
| (KFmoc)WK(MetO$_2$)-NH$_2$ | 46 |
| (KFmoc)WK(aABA)-NH$_2$ | 48 |
| (KFmoc)WK(Cys[ACM])-NH$_2$ | 49 |
| (KFmoc)WK(Bala)-NH$_2$ | 51 |
| (KFmoc)WK(aAIB)-NH$_2$ | 57 |
| (KFmoc)WK(Hyp)-NH$_2$ | 62 |
| (KFmoc)WK(Thiopro)-NH$_2$ | 64 |
| (KFmoc)WK(gABA)-NH$_2$ | 65 |
| (KFmoc)WK(dOrn)-NH$_2$ | 69 |
| (KFmoc)WK(Orn)-NH$_2$ | 100 |
| (KFmoc)WK(7aHa)-NH$_2$ | 104 |

TABLE 3

ANTIMICROBIAL ACTIVITY AGAINST *E. COLI* OF (KFmoc)WYZ-NH$_2$

| | $IC_{50}$ (μg/ml) | | $IC_{50}$ (μg/ml) |
|---|---|---|---|
| (KFmoc)WYR-NH$_2$ | 23 | (KFmoc)WYr-NH$_2$ | 16 |
| (KFmoc)WYK-NH$_2$ | 35 | (KFmoc)WYk-NH$_2$ | 18 |
| (KFmoc)WYH-NH$_2$ | 35 | (KFmoc)Wyh-NH$_2$ | 40 |
| (KFmoc)WYX-NH$_2$ | 42 | (KFmoc)WYX-NH$_2$ | 42 |
| (KFmoc)WYP-NH$_2$ | 66 | (KFmoc)WYt-NH$_2$ | 81 |
| (KFmoc)WYT-NH$_2$ | 71 | (KFmoc)WYp-NH$_2$ | 84 |
| (KFmoc)WYG-NH$_2$ | 72 | (KFmoc)WYa-NH$_2$ | 87 |
| (KFmoc)WYS-NH$_2$ | 94 | (KFmoc)WYv-NH$_2$ | 102 |
| (KFmoc)WXX-NH$_2$ | 32 | (KFmoc)WYs-NH$_2$ | 106 |
| (KFmoc)XXX-NH$_2$ | 179 | (KFmoc)WYf-NH$_2$ | 116 |
| | | (KFmoc)WYl-NH$_2$ | 123 |

| | $IC_{50}$ (μg/m) |
|---|---|
| (KFmoc)WY(Orn)-NH$_2$ | 29 |
| (KFmoc)WY(dOrn)-NH$_2$ | 35 |
| (KFmoc)WYX-NH$_2$ | 42 |
| (KFmoc)WY(aABA)-NH$_2$ | 43 |
| (KFmoc)WY(KCBZ)-NH$_2$ | 59 |
| (KFmoc)WY(aAIB)-NH$_2$ | 92 |

TABLE 4

ANTIMICROBIAL ACTIVITY AGAINST *E. COLI* OF (KFmoc)WfZ-NH$_2$

| | $IC_{50}$ (μg/ml) | | $IC_{50}$ (μg/ml) |
|---|---|---|---|
| (KFmoc)WfL-NH$_2$ | 10 | (KFmoc)Wfr-NH$_2$ | 15 |
| (KFmoc)WfP-NH$_2$ | 17 | (KFmoc)WfX-NH$_2$ | 20 |
| (KFmoc)WfR-NH$_2$ | 19 | (KFmoc)Wff-NH$_2$ | 21 |
| (KFmoc)WfX-NH$_2$ | 20 | (KFmoc)Wfw-NH$_2$ | 27 |
| (KFmoc)WfK-NH$_2$ | 76 | (KFmoc)Wfl-NH$_2$ | 28 |
| (KFmoc)WfH-NH$_2$ | 85 | (KFmoc)Wfp-NH$_2$ | 30 |
| (KFmoc)WXX-NH$_2$ | 32 | (KFmoc)Wfm-NH$_2$ | 35 |
| (KFmoc)XXX-NH$_2$ | 179 | (KFmoc)Wft-NH$_2$ | 51 |
| | | (KFmoc)Wfv-NH$_2$ | 73 |
| | | (KFmoc)Wfh-NH$_2$ | 73 |
| | | (KFmoc)Wfq-NH$_2$ | 76 |
| | | (KFmoc)Wfc-NH$_2$ | 86 |

TABLE 4-continued

ANTIMICROBIAL ACTIVITY AGAINST E. COLI OF (KFmoc)WfZ-NH₂

|  | (KFmoc)Wfk-NH₂ | 101 |
| --- | --- | --- |
|  |  | IC₅₀ (μg/m) |
| (KFmoc)Wf(Thiopro)-NH₂ |  | 16 |
| (KFmoc)Wf(dOrn)-NH₂ |  | 19 |
| (KFmoc)WfX-NH₂ |  | 20 |
| (KFmoc)Wf(aABA)-NH₂ |  | 21 |
| (KFmoc)Wf(Nve)-NH₂ |  | 22 |
| (KFmoc)Wf(aAIB)-NH₂ |  | 27 |
| (KFmoc)Wf(KCBZ)-NH₂ |  | 28 |
| (KFmoc)Wf(Orn)-NH₂ |  | 30 |
| (KFmoc)Wf(Hyp)-NH₂ |  | 44 |
| (KFmoc)Wf(Nle)-NH₂ |  | 46 |
| (KFmoc)Wf(MetO₂)-NH₂ |  | 62 |
| (KFmoc)Wf(gABA)-NH₂ |  | 65 |
| (KFmoc)Wf(Bala)-NH₂ |  | 70 |
| (KFmoc)Wf(NO₂F)-NH₂ |  | 88 |

TABLE 5

ANTIMICROBIAL ACTIVITY AGAINST E. COLI OF (KFmoc)ciZ-NH₂

|  | IC₅₀ (μg/ml) |  | IC₅₀ (μg/ml) |
| --- | --- | --- | --- |
| (KFmoc)ciT-NH₂ | 17 | (KFmoc)cir-NH₂ | 18 |
| (KFmoc)ciR-NH₂ | 22 | (KFmoc)ciX-NH₂ | 26 |
| (KFmoc)ciL-NH₂ | 24 | (KFmoc)cik-NH₂ | 27 |
| (KFmoc)ciX-NH₂ | 26 | (KFmoc)cip-NH₂ | 31 |
| (KFmoc)ciP-NH₂ | 28 | (KFmoc)cit-NH₂ | 56 |
| (KFmoc)ciH-NH₂ | 33 | (KFmoc)ciw-NH₂ | 61 |
| (KFmoc)ciK-NH₂ | 35 | (KFmoc)cic-NH₂ | 61 |
| (KFmoc)ciW-NH₂ | 42 |  |  |
| (KFmoc)ciI-NH₂ | 45 |  |  |
| (KFmoc)ciF-NH₂ | 47 |  |  |
| (KFmoc)ciA-NH₂ | 50 |  |  |
| (KFmoc)ciV-NH₂ | 62 |  |  |
| (KFmoc)ciM-NH₂ | 75 |  |  |
| (KFmoc)cZZ-NH₂ | 58 |  |  |
| (KFmoc)ZZZ-NH₂ | 179 |  |  |

|  | IC₅₀ (μg/m) |
| --- | --- |
| (KFmoc)ci(KCBZ)-NH₂ | 15 |
| (KFmoc)ci(dOrn)-NH₂ | 20 |
| (KFmoc)ci(aAIB)-NH₂ | 22 |
| (KFmoc)ci(Thiopro)-NH₂ | 25 |
| (KFmoc)ci(aABA)-NH₂ | 25 |
| (KFmoc)ciX-NH₂ | 26 |
| (KFmoc)ci(Orn)-NH₂ | 31 |
| (KFmoc)ci(Nve)-NH₂ | 51 |
| (KFmoc)ci(Hyp)-NH₂ | 52 |
| (KFmoc)ci(Nle)-NH₂ | 78 |
| (KFmoc)ci(KFmoc)-NH₂ | 97 |

TABLE 6

ANTIMICROBIAL ACTIVITY AGAINST S. AUREUS OF (KFmoc)WKZ-NH₂

|  | IC₅₀ (μg/ml) |  | IC₅₀ (μg/ml) |
| --- | --- | --- | --- |
| (KFmoc)WKW-NH₂ | 4 | (KFmoc)WKw-NH₂ | 4 |
| (KFmoc)WKC-NH₂ | 4 | (KFmoc)WKc-NH₂ | 4 |
| (KFmoc)WKF-NH₂ | 5 | (KFmoc)WKl-NH₂ | 5 |
| (KFmoc)WKS-NH₂ | 5 | (KFmoc)WKs-NH₂ | 6 |
| (KFmoc)WKM-NH₂ | 5 | (KFmoc)WKh-NH₂ | 6 |
| (KFmoc)WKY-NH₂ | 5 | (KFmoc)WKy-NH₂ | 7 |
| (KFmoc)WKK-NH₂ | 5 | (KFmoc)WKr-NH₂ | 7 |
| (KFmoc)WKT-NH₂ | 7 | (KFmoc)WKa-NH₂ | 7 |
| (KFmoc)WKR-NH₂ | 7 | (KFmoc)WKq-NH₂ | 7 |
| (KFmoc)WKG-NH₂ | 7 | (KFmoc)WKm-NH₂ | 7 |
| (KFmoc)WKX-NH₂ | 7 | (KFmoc)WKX-NH₂ | 7 |
| (KFmoc)WKL-NH₂ | 8 | (KFmoc)WKp-NH₂ | 8 |
| (KFmoc)WKH-NH₂ | 8 | (KFmoc)WKk-NH₂ | 8 |
| (KFmoc)WKV-NH₂ | 8 | (KFmoc)WKi-NH₂ | 9 |
| (KFmoc)WKI-NH₂ | 9 | (KFmoc)WKv-NH₂ | 9 |
| (KFmoc)WKN-NH₂ | 9 | (KFmoc)WKt-NH₂ | 10 |
| (KFmoc)WKA-NH₂ | 9 | (KFmoc)WKf-NH₂ | 10 |
| (KFmoc)WKQ-NH₂ | 10 | (KFmoc)WKn-NH₂ | 10 |
| (KFmoc)WKP-NH₂ | 13 | (KFmoc)WKd-NH₂ | 14 |
| (KFmoc)WKD-NH₂ | 25 | (KFmoc)WKe-NH₂ | 43 |
| (KFmoc)WKE-NH₂ | 37 |  |  |
| (KFmoc)WXX-NH₂ | 18 |  |  |
| (KFmoc)XXX-NH₂ | 44 |  |  |

|  | IC₅₀ (μg/ml) |
| --- | --- |
| (KFmoc)WK(NO₂F)-NH₂ | 5 |
| (KFmoc)WK(Orn)-NH₂ | 5 |
| (KFmoc)WK(dOrn)-NH₂ | 5 |
| (KFmoc)WK(aABA)-NH, | 6 |
| (KFmoc)WK(Nle)-NH₂ | 7 |
| (KFmoc)WKX-NH₂ | 7 |
| (KFmoc)WK(KFmoc)-NH₂ | 9 |
| (KFmoc)WK(aAIB)-NH₂ | 9 |
| (KFmoc)WK(KCBZ)-NH₂ | 9 |
| (KFmoc)WK(MetO₂)-NH₂ | 9 |
| (KFmoc)WK(Hyp)-NH₂ | 10 |
| (KFmoc)WK(Nve)-NH₂ | 10 |
| (KFmoc)WK(Cys[ACM])-NH₂ | 11 |
| (KFmoc)WK(Bala)-NH₂ | 11 |
| (KFmoc)WK(Thiopro)-NH₂ | 12 |
| (KFmoc)WK(bAsp)-NH₂ | 15 |
| (KFmoc)WK(7aHa)-NH₂ | 17 |
| (KFmoc)WK(gGlu)-NH₂ | 18 |
| (KFmoc)WK(gABA)-NH₂ | 18 |
| (KFmoc)WK(eAca)-NH₂ | 40 |

TABLE 7

ANTIMICROBIAL ACTIVITY AGAINST S. AUREUS OF (KFmoc)WYU-NH₂

|  | IC₅₀ (μg/ml) |  | IC₅₀ (μg/ml) |
| --- | --- | --- | --- |
| (KFmoc)WYR-NH₂ | 5 | (KFmoc)Wyr-NH₂ | 4 |
| (KFmoc)WYK-NH₂ | 6 | (KFmoc)WYs-NH₂ | 5 |
| (KFmoc)WYL-NH₂ | 7 | (KFmoc)WYa-NH₂ | 5 |
| (KFmoc)WYW-NH₂ | 7 | (KFmoc)WYk-NH₂ | 5 |
| (KFmoc)WYT-NH₂ | 8 | (KFmoc)WYp-NH₂ | 5 |
| (KFmoc)WYH-NH₂ | 8 | (KFmoc)WYn-NH₂ | 6 |
| (KFmoc)WYY-NH₂ | 8 | (KFmoc)WYh-NH₂ | 7 |
| (KFmoc)WYX-NH₂ | 8 | (KFmoc)WYl-NH₂ | 8 |
| (KFmoc)WYP-NH₂ | 9 | (KFmoc)WYX-NH₂ | 8 |
| (KFmoc)WYV-NH₂ | 9 | (KFmoc)WYm-NH₂ | 9 |
| (KFmoc)WYG-NH₂ | 9 | (KFmoc)WYv-NH₂ | 9 |
| (KFmoc)WYA-NH₂ | 10 | (KFmoc)WYt-NH₂ | 9 |
| (KFmoc)WYN-NH₂ | 11 | (KFmoc)WYq-NH₂ | 10 |
| (KFmoc)WYS-NH₂ | 11 | (KFmoc)WYi-NH₂ | 12 |
| (KFmoc)WYQ-NH₂ | 12 | (KFmoc)WYf-NH₂ | 12 |

TABLE 7-continued
ANTIMICROBIAL ACTIVITY AGAINST S. AUREUS OF (KFmoc)WYU-NH$_2$

| | | | |
|---|---|---|---|
| (KFmoc)WYM-NH$_2$ | 12 | (KFmoc)WYw-NH$_2$ | 16 |
| (KFmoc)WYI-NH$_2$ | 15 | (KFmoc)WYc-NH$_2$ | 21 |
| (KFmoc)WYC-NH$_2$ | 15 | (KFmoc)WYy-NH$_2$ | 26 |
| (KFmoc)WYF-NH$_2$ | 17 | | |
| (KFmoc)WXX-NH$_2$ | 18 | | |
| (KFmoc)XXX-NH$_2$ | 44 | | |

| | IC$_{50}$ (μg/m) |
|---|---|
| (KFmoc)WY(aABA)-NH$_2$ | 4 |
| (KFmoc)WY(7aHa)-NH$_2$ | 5 |
| (KFmoc)WY(dOrn)-NH$_2$ | 5 |
| (KFmoc)WY(Orn)-NH$_2$ | 6 |
| (KFmoc)WYX-NH$_2$ | 8 |
| (KFmoc)WY(KCBZ)-NH$_2$ | 9 |
| (KFmoc)WY(Hyp)-NH$_2$ | 9 |
| (KFmoc)WY(aAIB)-NH$_2$ | 10 |
| (KFmoc)WY(Nle)-NH$_2$ | 14 |
| (KFmoc)WY(eAca)-NH$_2$ | 15 |
| (KFmoc)WY(NO$_2$F)-NH$_2$ | 15 |
| (KFmoc)WY(Bala)-NH$_2$ | 18 |
| (KFmoc)WY(Thiopro)-NH$_2$ | 20 |
| (KFmoc)WY(Nve)-NH$_2$ | 20 |
| (KFmoc)WY(Cys[ACM])-NH$_2$ | 23 |
| (KFmoc)WY(gABA)-NH$_2$ | 35 |
| (KFmoc)WY(MetO$_2$)-NH$_2$ | 40 |

TABLE 8
ANTIMICROBIAL ACTIVITY AGAINST S. AUREUS OF (KFmoc)WfZ-NH$_2$

| | IC$_{50}$ (μg/ml) | | IC$_{50}$ (μg/ml) |
|---|---|---|---|
| (KFmoc)WfR-NH$_2$ | 2 | (KFmoc)Wfl-NH$_2$ | 2 |
| (KFmoc)WfL-NH$_2$ | 4 | (KFmoc)Wfw-NH$_2$ | 2 |
| (KFmoc)WfP-NH$_2$ | 4 | (KFmoc)Wfr-NH$_2$ | 2 |
| (KFmoc)WfX-NH$_2$ | 4 | (KFmoc)Wfi-NH$_2$ | 4 |
| (KFmoc)WfK-NH$_2$ | 6 | (KFmoc)WfX-NH$_2$ | 4 |
| (KFmoc)WfN-NH$_2$ | 8 | (KFmoc)Wff-NH$_2$ | 5 |
| (KFmoc)WfH-NH$_2$ | 9 | (KFmoc)Wfm-NH$_2$ | 5 |
| (KFmoc)WfT-NH$_2$ | 9 | (KFmoc)Wfv-NH$_2$ | 6 |
| (KFmoc)WfV-NH$_2$ | 13 | (KFmoc)Wfp-NH$_2$ | 7 |
| (KFmoc)WfS-NH$_2$ | 13 | (KFmoc)Wft-NH$_2$ | 7 |
| (KFmoc)WfA-NH$_2$ | 15 | (KFmoc)Wfa-NH$_2$ | 8 |
| (KFmoc)WfM-NH$_2$ | 18 | (KFmoc)Wfs-NH$_2$ | 9 |
| (KFmoc)WfF-NH$_2$ | 21 | (KFmoc)Wfh-NH$_2$ | 9 |
| (KFmoc)WfC-NH$_2$ | 22 | (KFmoc)Wfk-NH$_2$ | 9 |
| (KFmoc)WfI-NH$_2$ | 26 | (KFmoc)Wfq-NH$_2$ | 10 |
| (KFmoc)WfY-NH$_2$ | 58 | (KFmoc)Wfy-NH$_2$ | 15 |
| (KFmoc)WXX-NH$_2$ | 18 | (KFmoc)Wfc-NH$_2$ | 18 |
| (KFmoc)XXX-NH$_2$ | 44 | (KFmoc)Wfn-NH$_2$ | 35 |

| | IC$_{50}$ (μg/m) |
|---|---|
| (KFmoc)Wf(KCBZ)-NH$_2$ | 3 |
| (KFmoc)Wf(Thiopro)-NH$_2$ | 3 |
| (KFmoc)Wf(dOrn)-NH$_2$ | 4 |
| (KFmoc)Wf(Orn)-NH$_2$ | 4 |
| (KFmoc)Wf(aAIB)-NH$_2$ | 4 |
| (KFmoc)WfX-NH$_2$ | 4 |
| (KFmoc)Wf(MetO$_2$)-NH$_2$ | 5 |
| (KFmoc)Wf(Hyp)-NH$_2$ | 5 |
| (KFmoc)Wf(Nve)-NH$_2$ | 6 |
| (KFmoc)Wf(aABA)-NH$_2$ | 6 |
| (KFmoc)Wf(7aHa)-NH$_2$ | 7 |
| (KFmoc)Wf(Nle)-NH$_2$ | 9 |
| (KFmoc)Wf(NO$_2$F)-NH$_2$ | 10 |
| (KFmoc)Wf(gABA)-NH$_2$ | 11 |
| (KFmoc)Wf(Bala)-NH$_2$ | 11 |
| (KFmoc)Wf(Cys[ACM])-NH$_2$ | 18 |

TABLE 9
ANTIMICROBIAL ACTIVITY AGAINST S. AUREUS OF (KFmoc)ciZ-NH$_2$

| | IC$_{50}$ (μg/ml) | | IC$_{50}$ (μg/ml) |
|---|---|---|---|
| (KFmoc)ciR-NH$_2$ | 4 | (KFmoc)cir-NH$_2$ | 3 |
| (KFmoc)ciK-NH$_2$ | 4 | (KFmoc)cik-NH$_2$ | 6 |
| (KFmoc)ciP-NH$_2$ | 5 | (KFmoc)cip-NH$_2$ | 8 |
| (KFmoc)ciM-NH$_2$ | 9 | (KFmoc)cil-NH$_2$ | 9 |
| (KFmoc)ciH-NH$_2$ | 9 | (KFmoc)ciX-NH$_2$ | 10 |
| (KFmoc)ciA-NH$_2$ | 9 | (KFmoc)cit-NH$_2$ | 14 |
| (KFmoc)ciW-NH$_2$ | 10 | (KFmoc)ciw-NH$_2$ | 14 |
| (KFmoc)ciT-NH$_2$ | 10 | (KFmoc)cim-NH$_2$ | 17 |
| (KFmoc)ciL-NH$_2$ | 10 | (KFmoc)cic-NH$_2$ | 17 |
| (KFmoc)ciX-NH$_2$ | 10 | (KFmoc)cif-NH$_2$ | 21 |
| (KFmoc)ciY-NH$_2$ | 13 | (KFmoc)ciy-NH$_2$ | 28 |
| (KFmoc)ciS-NH$_2$ | 16 | (KFmoc)cis-NH$_2$ | 29 |
| (KFmoc)ciI-NH$_2$ | 19 | | |
| (KFmoc)ciF-NH$_2$ | 20 | | |
| (KFmoc)ciN-NH$_2$ | 22 | | |
| (KFmoc)ciV-NH$_2$ | 23 | | |
| (KFmoc)cXX-NH$_2$ | 23 | | |
| (KFmoc)XXX-NH$_2$ | 44 | | |

| | IC$_{50}$ (μg/m) |
|---|---|
| (KFmoc)ci(aAIB)-NH$_2$ | 4 |
| (KFmoc)ci(Orn)-NH$_2$ | 4 |
| (KFmoc)ci(dOrn)-NH$_2$ | 4 |
| (KFmoc)ci(KCBZ)-NH$_2$ | 5 |
| (KFmoc)ci(aABA)-NH$_2$ | 5 |
| (KFmoc)ci(Hyp)-NH$_2$ | 8 |
| (KFmoc)ci(Thiopro)-NH$_2$ | 9 |
| (KFmoc)ciX-NH$_2$ | 10 |
| (KFmoc)ci(KFmoc)-NH$_2$ | 13 |
| (KFmoc)ci(7aHa)-NH$_2$ | 15 |
| (KFmoc)ci(eAca)-NH$_2$ | 16 |
| (KFmoc)ci(Nve)-NH$_2$ | 16 |
| (KFmoc)ci(Nle)-NH$_2$ | 22 |
| (KFmoc)ci(NO$_2$F)-NH$_2$ | 25 |

TABLE 10
ANTIMICROBIAL ACTIVITY AGAINST S. SANGUIS OF (KFmoc)WKZ-NH$_2$

| | IC$_{50}$ (μg/ml) | | IC$_{50}$ (μg/ml) |
|---|---|---|---|
| (KFmoc)WKW-NH$_2$ | 3 | (KFmoc)WKc-NH$_2$ | 4 |
| (KFmoc)WKC-NH$_2$ | 4 | (KFmoc)WKw-NH$_2$ | 4 |
| (KFmoc)WKY-NH$_2$ | 5 | (KFmoc)WKr-NH$_2$ | 5 |
| (KFmoc)WKS-NH$_2$ | 5 | (KFmoc)WKp-NH$_2$ | 5 |
| (KFmoc)WKL-NH$_2$ | 5 | (KFmoc)WKl-NH$_2$ | 5 |
| (KFmoc)WKM-NH$_2$ | 5 | (KFmoc)WKh-NH$_2$ | 6 |
| (KFmoc)WKK-NH$_2$ | 5 | (KFmoc)WKs-NH$_2$ | 6 |
| (KFmoc)WKT-NH$_2$ | 5 | (KFmoc)WKf-NH$_2$ | 6 |
| (KFmoc)WKF-NH$_2$ | 6 | (KFmoc)WKq-NH$_2$ | 7 |
| (KFmoc)WKG-NH$_2$ | 6 | (KFmoc)WKk-NH$_2$ | 7 |
| (KFmoc)WKH-NH$_2$ | 6 | (KFmoc)WKt-NH$_2$ | 7 |
| (KFmoc)WKR-NH$_2$ | 7 | (KFmoc)WKm-NH$_2$ | 7 |
| (KFmoc)WKA-NH$_2$ | 8 | (KFmoc)WKy-NH$_2$ | 8 |
| (KFmoc)WKN-NH$_2$ | 8 | (KFmoc)WKi-NH$_2$ | 8 |
| (KFmoc)WKQ-NH$_2$ | 9 | (KFmoc)WKa-NH$_2$ | 8 |
| (KFmoc)WKP-NH$_2$ | 9 | (KFmoc)WKn-NH$_2$ | 8 |
| (KFmoc)WKI-NH$_2$ | 9 | (KFmoc)WKX-NH$_2$ | 9 |
| (KFmoc)WKV-NH$_2$ | 9 | (KFmoc)WKv-NH$_2$ | 10 |
| (KFmoc)WKX-NH$_2$ | 9 | (KFmoc)WKd-NH$_2$ | 19 |

TABLE 10-continued

ANTIMICROBIAL ACTIVITY AGAINST S. SANGUIS OF (KFmoc)WKZ-NH$_2$

| | | | |
|---|---|---|---|
| (KFmoc)WKD-NH$_2$ | 31 | (KFmoc)WKe-NH$_2$ | 50 |
| (KFmoc)WXX-NH$_2$ | 10 | | |
| (KFmoc)XXX-NH$_2$ | 44 | | |

| | IC$_{50}$ (μg/ml) |
|---|---|
| (KFmoc)WK(Orn)-NH$_2$ | 5 |
| (KFmoc)WK(dOrn)-NH$_2$ | 5 |
| (KFmoc)WK(NO$_2$F)-NH$_2$ | 5 |
| (KFmoc)WK(Nle)-NH$_2$ | 6 |
| (KFmoc)WK(aABA)-NH$_2$ | 7 |
| (KFmoc)WK(aAIB)-NH$_2$ | 8 |
| (KFmoc)WK(MetO$_2$)-NH$_2$ | 9 |
| (KFmoc)WK(KCBZ)-NH$_2$ | 9 |
| (KFmoc)WY(Nve)-NH$_2$ | 9 |
| (KFmoc)WK(Bala)-NH$_2$ | 9 |
| (KFmoc)WKX-NH$_2$ | 9 |
| (KFmoc)WK(Hyp)-NH$_2$ | 10 |
| (KFmoc)WK(Thiopro)-NH$_2$ | 11 |
| (KFmoc)WK(Cys[ACM])-NH$_2$ | 11 |
| (KFmoc)WK(KFmoc)-NH$_2$ | 12 |
| (KFmoc)WK(gABA)-NH$_2$ | 14 |
| (KFmoc)WK(7aHa)-NH$_2$ | 19 |
| (KFmoc)WK(bAsp)-NH$_2$ | 19 |
| (KFmoc)WK(eAca)-NH$_2$ | 31 |
| (KFmoc)WK(gGlu)-NH$_2$ | 32 |

TABLE 11

ANTIMICROBIAL ACTIVITY AGAINST S. SANGUIS OF (KFmoc)WYZ-NH$_2$

| | IC$_{50}$ (μg/ml) | | IC$_{50}$ (μg/ml) |
|---|---|---|---|
| (KFmoc)WYR-NH$_2$ | 5 | (KFmoc)WYr-NH$_2$ | 4 |
| (KFmoc)WYK-NH$_2$ | 6 | (KFmoc)WYa-NH$_2$ | 5 |
| (KFmoc)WYT-NH$_2$ | 8 | (KFmoc)WYp-NH$_2$ | 5 |
| (KFmoc)WYL-NH$_2$ | 8 | (KFmoc)Wyk-NH$_2$ | 5 |
| (KFmoc)WYH-NH$_2$ | 9 | (KFmoc)WYs-NH$_2$ | 5 |
| (KFmoc)WYP-NH$_2$ | 9 | (KFmoc)WYv-NH$_2$ | 7 |
| (KFmoc)WYS-NH$_2$ | 9 | (KFmoc)WYl-NH$_2$ | 8 |
| (KFmoc)WYW-NH$_2$ | 9 | (KFmoc)WYh-NH$_2$ | 8 |
| (KFmoc)WYG-NH$_2$ | 9 | (KFmoc)WYm-NH$_2$ | 8 |
| (KFmoc)WYY-NH$_2$ | 10 | (KFmoc)WYt-NH$_2$ | 8 |
| (KFmoc)WYV-NH$_2$ | 10 | (KFmoc)WYn-NH$_2$ | 8 |
| (KFmoc)WYM-NH$_2$ | 11 | (KFmoc)WYq-NH$_2$ | 11 |
| (KFmoc)WYN-NH$_2$ | 12 | (KFmoc)WYi-NH$_2$ | 12 |
| (KFmoc)WYA-NH$_2$ | 12 | (KFmoc)WYX-NH$_2$ | 12 |
| (KFmoc)WYX-NH$_2$ | 12 | (KFmoc)WYf-NH$_2$ | 13 |
| (KFmoc)WYQ-NH$_2$ | 13 | (KFmoc)WYw-NH$_2$ | 21 |
| (KFmoc)WYC-NH$_2$ | 20 | (KFmoc)WYy-NH$_2$ | 32 |
| (KFmoc)WYF-NH$_2$ | 21 | (KFmoc)WYc-NH$_2$ | 42 |
| (KFmoc)WYI-NH$_2$ | 53 | | |
| (KFmoc)WXX-NH$_2$ | 10 | | |
| (KFmoc)XXX-NH$_2$ | 44 | | |

| | IC$_{50}$ (μg/m) |
|---|---|
| (KFmoc)WY(aABA)-NH$_2$ | 5 |
| (KFmoc)WY(Orn)-NH$_2$ | 7 |
| (KFmoc)WY(dOrn)-NH$_2$ | 7 |
| (KFmoc)WY(aAIB)-NH$_2$ | 8 |
| (KFmoc)WY(KCBZ)-NH$_2$ | 9 |
| (KFmoc)WY(Hyp)-NH$_2$ | 10 |
| (KFmoc)WYX-NH$_2$ | 12 |
| (KFmoc)WY(7aHa)-NH$_2$ | 14 |
| (KFmoc)WY(eAca)-NH$_2$ | 15 |
| (KFmoc)WY(Nle)-NH$_2$ | 17 |

TABLE 11-continued

ANTIMICROBIAL ACTIVITY AGAINST S. SANGUIS OF (KFmoc)WYZ-NH$_2$

| | |
|---|---|
| (KFmoc)WY(Nve)-NH$_2$ | 18 |
| (KFmoc)WY(NO$_2$F)-NH$_2$ | 24 |
| (KFmoc)WY(Bala)-NH$_2$ | 26 |
| (KFmoc)WY(gABA)-NH$_2$ | 27 |
| (KFmoc)WY(Cys[ACM])-NH$_2$ | 28 |
| (KFmoc)WY(Thiopro)-NH$_2$ | 36 |

TABLE 12

ANTIMICROBIAL ACTIVITY AGAINST S. SANGUIS OF (KFmoc)WfZ-NH$_2$

| | IC$_{50}$ (μg/ml) | | IC$_{50}$ (μg/ml) |
|---|---|---|---|
| (KFmoc)WfR-NH$_2$ | 2 | (KFmoc)Wfl-NH$_2$ | 2 |
| (KFmoc)WfL-NH$_2$ | 4 | (KFmoc)Wfw-NH$_2$ | 2 |
| (KFmoc)WfP-NH$_2$ | 4 | (KFmoc)Wfr-NH$_2$ | 2 |
| (KFmoc)WfK-NH$_2$ | 5 | (KFmoc)Wfi-NH$_2$ | 4 |
| (KFmoc)WfX-NH$_2$ | 6 | (KFmoc)Wff-NH$_2$ | 5 |
| (KFmoc)WfH-NH$_2$ | 8 | (KFmoc)Wfp-NH$_2$ | 6 |
| (KFmoc)WfA-NH$_2$ | 10 | (KFmoc)WfX-NH$_2$ | 6 |
| (KFmoc)WfN-NH$_2$ | 10 | (KFmoc)Wfv-NH$_2$ | 7 |
| (KFmoc)WfI-NH$_2$ | 15 | (KFmoc)Wft-NH$_2$ | 7 |
| (KFmoc)WfV-NH$_2$ | 16 | (KFmoc)Wfs-NH$_2$ | 8 |
| (KFmoc)WfM-NH$_2$ | 19 | (KFmoc)Wfk-NH$_2$ | 9 |
| (KFmoc)WfF-NH$_2$ | 20 | (KFmoc)Wfm-NH$_2$ | 9 |
| (KFmoc)WfS-NH$_2$ | 21 | (KFmoc)Wfa-NH$_2$ | 9 |
| (KFmoc)WfT-NH$_2$ | 24 | (KFmoc)Wfh-NH$_2$ | 9 |
| (KFmoc)WfC-NH$_2$ | 31 | (KFmoc)Wfq-NH$_2$ | 15 |
| (KFmoc)WfY-NH$_2$ | 36 | (KFmoc)Wfy-NH$_2$ | 17 |
| (KFmoc)WXX-NH$_2$ | 10 | (KFmoc)Wfc-NH$_2$ | 20 |
| (KFmoc)XXX-NH$_2$ | 44 | | |

| | IC$_{50}$ (μg/m) |
|---|---|
| (KFmoc)Wf(Thiopro)-NH$_2$ | 3 |
| (KFmoc)Wf(Orn)-NH$_2$ | 4 |
| (KFmoc)Wf(KCBZ)-NH$_2$ | 4 |
| (KFmoc)Wf(aAIB)-NH$_2$ | 4 |
| (KFmoc)Wf(dOrn)-NH$_2$ | 4 |
| (KFmoc)Wf(Nve)-NH$_2$ | 5 |
| (KFmoc)WfX-NH$_2$ | 6 |
| (KFmoc)Wf(aABA)-NH$_2$ | 7 |
| (KFmoc)Wf(MetO$_2$)-NH$_2$ | 8 |
| (KFmoc)Wf(Hyp)-NH$_2$ | 8 |
| (KFmoc)Wf(gABA)-NH$_2$ | 9 |
| (KFmoc)Wf(Bala)-NH$_2$ | 10 |
| (KFmoc)Wf(7aHa)-NH$_2$ | 10 |
| (KFmoc)Wf(NO$_2$F)-NH$_2$ | 11 |
| (KFmoc)Wf(Nle)-NH$_2$ | 12 |
| (KFmoc)Wf(Cys[ACM])-NH$_2$ | 30 |
| (KFmoc)Wf(eAca)-NH$_2$ | 60 |

TABLE 13

ANTIMICROBIAL ACTIVITY AGAINST S. SANGUIS OF (KFmoc)ciZ-NH$_2$

| | IC$_{50}$ (μg/ml) | | IC$_{50}$ (μg/ml) |
|---|---|---|---|
| (KFmoc)ciR-NH$_2$ | 3 | (KFmoc)cir-NH$_2$ | 2 |
| (KFmoc)ciP-NH$_2$ | 4 | (KFmoc)cik-NH$_2$ | 4 |
| (KFmoc)ciK-NH$_2$ | 4 | (KFmoc)cip-NH$_2$ | 8 |
| (KFmoc)ciH-NH$_2$ | 5 | (KFmoc)ciX-NH$_2$ | 14 |
| (KFmoc)ciM-NH$_2$ | 10 | (KFmoc)ciw-NH$_2$ | 19 |
| (KFmoc)ciW-NH$_2$ | 12 | (KFmoc)cis-NH$_2$ | 22 |
| (KFmoc)ciX-NH$_2$ | 14 | (KFmoc)cit-NH$_2$ | 27 |
| (KFmoc)ciT-NH$_2$ | 15 | (KFmoc)cim-NH$_2$ | 28 |
| (KFmoc)ciL-NH$_2$ | 16 | (KFmoc)cil-NH$_2$ | 32 |
| (KFmoc)ciA-NH$_2$ | 16 | (KFmoc)ciy-NH$_2$ | 43 |
| (KFmoc)ciY-NH$_2$ | 16 | (KFmoc)cih-NH$_2$ | 50 |
| (KFmoc)ciF-NH$_2$ | 16 | (KFmoc)cic-NH$_2$ | 53 |
| (KFmoc)ciS-NH$_2$ | 22 | (KFmoc)cia-NH$_2$ | 59 |
| (KFmoc)ciG-NH$_2$ | 23 | (KFmoc)ciV-NH$_2$ | 37 |
| (KFmoc)ciI-NH$_2$ | 38 | | |
| (KFmoc)ciN-NH$_2$ | 47 | | |
| (KFmoc)cXX-NH$_2$ | 13 | | |

TABLE 13-continued

ANTIMICROBIAL ACTIVITY AGAINST *S. SANGUIS* OF (KFmoc)ciZ-NH$_2$

| | |
|---|---|
| (KFmoc)XXX-NH$_2$ | 44 |

| | IC$_{50}$ (μg/m) |
|---|---|
| (KFmoc)ci(Orn)-NH$_2$ | 2 |
| (KFmoc)ci(dOrn)-NH$_2$ | 2 |
| (KFmoc)ci(KCBZ)-NH$_2$ | 3 |
| (KFmoc)ci(aABA)-NH$_2$ | 4 |
| (KFmoc)ci(aAIB)-NH$_2$ | 5 |
| (KFmoc)ci(Thiopro)-NH$_2$ | 6 |
| (KFmoc)ci(Hyp)-NH$_2$ | 8 |
| (KFmoc)ciX-NH$_2$ | 14 |
| (KFmoc)ci(KFmoc)-NH$_2$ | 15 |
| (KFmoc)ci(Nve)-NH$_2$ | 19 |
| (KFmoc)ci(Nle)-NH$_2$ | 28 |
| (KFmoc)ci(NO$_2$F)-NH$_2$ | 36 |
| (KFmoc)ci(eAca)-NH$_2$ | 42 |
| (KFmoc)ci(7aHa)-NH$_2$ | 53 |

TABLE 14

ANTIFUNGAL ACTIVITY AGAINST *C. ALBICANS* OF (KFmoc)WKZ-NH$_2$

| | IC$_{50}$ (μg/ml) | | IC$_{50}$ (μg/ml) |
|---|---|---|---|
| (KFmoc)WKF-NH$_2$ | 65 | (KFmoc)WKr-NH$_2$ | 98 |
| (KFmoc)WKI-NH$_2$ | 79 | (KFmoc)WKw-NH$_2$ | 116 |
| (KFmoc)WKL-NH$_2$ | 97 | (KFmoc)WKl-NH$_2$ | 121 |
| (KFmoc)WKR-NH$_2$ | 108 | (KFmoc)WKk-NH$_2$ | 126 |
| (KFmoc)WKW-NH$_2$ | 124 | (KFmoc)WKf-NH$_2$ | 133 |
| (KFmoc)WKY-NH$_2$ | 138 | (KFmoc)WKy-NH$_2$ | 144 |
| (KFmoc)WKV-NH$_2$ | 148 | (KFmoc)WKh-NH$_2$ | 156 |
| (KFmoc)WKX-NH$_2$ | 163 | (KFmoc)WKm-NH$_2$ | 163 |
| (KFmoc)WKK-NH$_2$ | 191 | (KFmoc)WKX-NH$_2$ | 163 |
| (KFmoc)WKM-NH$_2$ | 213 | (KFmoc)WKv-NH$_2$ | 187 |
| (KFmoc)WKG-NH$_2$ | 217 | (KFmoc)WKa-NH$_2$ | 200 |
| (KFmoc)WKS-NH$_2$ | 218 | (KFmoc)WKi-NH$_2$ | 209 |
| (KFmoc)WKH-NH$_2$ | 221 | (KFmoc)WKs-NH$_2$ | 214 |
| (KFmoc)WKT-NH$_2$ | 260 | (KFmoc)WKn-NH$_2$ | 233 |
| (KFmoc)WKC-NH$_2$ | 269 | (KFmoc)WKc-NH$_2$ | 243 |
| (KFmoc)WKQ-NH$_2$ | 292 | (KFmoc)WKp-NH$_2$ | 251 |
| (KFmoc)WKN-NH$_2$ | 323 | (KFmoc)WKq-NH$_2$ | 291 |
| (KFmoc)WKA-NH$_2$ | 333 | (KFmoc)WKt-NH$_2$ | 292 |
| (KFmoc)WKP-NH$_2$ | 338 | | |
| (KFmoc)WXX-NH$_2$ | 246 | | |
| (KFmoc)XXX-NH$_2$ | 770 | | |

| | IC$_{50}$ (μg/ml) |
|---|---|
| (KFmoc)WK(Nle)-NH$_2$ | 74 |
| (KFmoc)WK(NO$_2$F)-NH$_2$ | 101 |
| (KFmoc)WK(Nve)-NH$_2$ | 158 |
| (KFmoc)WK(KCBZ)-NH$_2$ | 161 |
| (KFmoc)WKX-NH$_2$ | 163 |
| (KFmoc)WY(Orn)-NH$_2$ | 177 |
| (KFmoc)WK(dOrn)-NH$_2$ | 196 |
| (KFmoc)WK(KFmoc)-NH$_2$ | 199 |
| (KFmoc)WK(Thiopro)-NH$_2$ | 223 |
| (KFmoc)WK(Bala)-NH$_2$ | 238 |
| (KFmoc)WK(aABA)-NH$_2$ | 245 |
| (KFmoc)WK(7aHa)-NH$_2$ | 252 |
| (KFmoc)WK(aAIB)-NH$_2$ | 281 |
| (KFmoc)WK(gABA)-NH$_2$ | 281 |
| (KFmoc)WK(MetO$_2$)-NH$_2$ | 294 |
| (KFmoc)WK(Cys[ACM])-NH$_2$ | 303 |
| (KFmoc)WK(eAca)-NH$_2$ | 328 |

TABLE 14-continued

ANTIFUNGAL ACTIVITY AGAINST *C. ALBICANS* OF (KFmoc)WKZ-NH$_2$

| | |
|---|---|
| (KFmoc)WK(Hyp)-NH$_2$ | 370 |

TABLE 15

ANTIFUNGAL ACTIVITY AGAINST *C. ALBICANS* OF (KFmoc)WYZ-NH$_2$

| | IC$_{50}$ (μg/ml) | | IC$_{50}$ (μg/ml) |
|---|---|---|---|
| (KFmoc)WYK-NH$_2$ | 101 | (KFmoc)WYr-NH$_2$ | 109 |
| (KFmoc)WYA-NH$_2$ | 120 | (KFmoc)WYk-NH$_2$ | 121 |
| (KFmoc)WYR-NH$_2$ | 124 | (KFmoc)WYt-NH$_2$ | 161 |
| (KFmoc)WYT-NH$_2$ | 152 | (KFmoc)WYp-NH$_2$ | 165 |
| (KFmoc)WYC-NH$_2$ | 159 | (KFmoc)WYh-NH$_2$ | 192 |
| (KFmoc)WYH-NH$_2$ | 165 | (KFmoc)WYX-NH$_2$ | 227 |
| (KFmoc)WYX-NH$_2$ | 227 | (KFmoc)WYa-NH$_2$ | 249 |
| (KFmoc)WYP-NH$_2$ | 255 | (KFmoc)WYs-NH$_2$ | 353 |
| (KFmoc)WYG-NH$_2$ | 282 | (KFmoc)WYv-NH$_2$ | 467 |
| (KFmoc)WXX-NH$_2$ | 246 | (KFmoc)WYq-NH$_2$ | 541 |
| (KFmoc)XXX-NH$_2$ | 770 | | |

| | IC$_{50}$ (μg/m) |
|---|---|
| (KFmoc)WY(Orn)-NH$_2$ | 183 |
| (KFmoc)WY(aABA)-NH$_2$ | 204 |
| (KFmoc)WYX-NH$_2$ | 227 |
| (KFmoc)WY(KCBZ)-NH$_2$ | 309 |
| (KFmoc)WY(dOrn)-NH$_2$ | 359 |

TABLE 16

ANTIFUNGAL ACTIVITY AGAINST *C. ALBICANS* OF (KFmoc)WfZ-NH$_2$

| | IC$_{50}$ (μg/ml) | | IC$_{50}$ (μg/ml) |
|---|---|---|---|
| (KFmoc)WfR-NH$_2$ | 101 | (KFmoc)Wfr-NH$_2$ | 42 |
| (KFmoc)WfP-NH$_2$ | 133 | (KFmoc)Wfl-NH$_2$ | 127 |
| (KFmoc)WfX-NH$_2$ | 157 | (KFmoc)Wfw-NH$_2$ | 143 |
| (KFmoc)WfH-NH$_2$ | 207 | (KFmoc)WfX-NH$_2$ | 157 |
| (KFmoc)WfK-NH$_2$ | 207 | (KFmoc)Wfk-NH$_2$ | 196 |
| (KFmoc)WfL-NH$_2$ | 267 | (KFmoc)Wfh-NH$_2$ | 338 |
| (KFmoc)WXX-NH$_2$ | 246 | (KFmoc)Wfp-NH$_2$ | 347 |
| (KFmoc)XXX-NH$_2$ | 770 | | |

| | IC$_{50}$ (μg/m) |
|---|---|
| (KFmoc)Wf(dOrn)-NH$_2$ | 54 |
| (KFmoc)Wf(KCBZ)-NH$_2$ | 58 |
| (KFmoc)Wf(aAIB)-NH$_2$ | 62 |
| (KFmoc)Wf(aABA)-NH$_2$ | 72 |
| (KFmoc)Wf(Orn)-NH$_2$ | 89 |
| (KFmoc)Wf(Hyp)-NH$_2$ | 95 |
| (KFmoc)Wf(Nve)-NH$_2$ | 118 |
| (KFmoc)Wf(MetO$_2$)-NH$_2$ | 150 |
| (KFmoc)WfX-NH$_2$ | 157 |
| (KFmoc)Wf(Bala)-NH$_2$ | 170 |
| (KFmoc)Wf(Thiopro)-NH$_2$ | 171 |
| (KFmoc)Wf(Nle)-NH$_2$ | 400 |

TABLE 17

ANTIFUNGAL ACTIVITY AGAINST *C. ALBICANS* OF (KFmoc)ciZ-NH$_2$

| | IC$_{50}$ (μg/ml) | | IC$_{50}$ (μg/ml) |
|---|---|---|---|
| (KFmoc)ciF-NH$_2$ | 90 | (KFmoc)cir-NH$_2$ | 114 |
| (KFmoc)ciL-NH$_2$ | 122 | (KFmoc)cik-NH$_2$ | 115 |
| (KFmoc)ciK-NH$_2$ | 161 | (KFmoc)cit-NH$_2$ | 194 |
| (KFmoc)ciR-NH$_2$ | 176 | (KFmoc)cih-NH$_2$ | 208 |

TABLE 17-continued
ANTIFUNGAL ACTIVITY AGAINST C. ALBICANS OF (KFmoc)ciZ-NH$_2$

| | | | |
|---|---|---|---|
| (KFmoc)ciH-NH$_2$ | 201 | (KFmoc)cil-NH$_2$ | 216 |
| (KFmoc)ciT-NH$_2$ | 228 | (KFmoc)cif-NH$_2$ | 218 |
| (KFmoc)ciI-NH$_2$ | 305 | (KFmoc)cii-NH$_2$ | 234 |
| (KFmoc)ciP-NH$_2$ | 216 | (KFmoc)cip-NH$_2$ | 270 |
| (KFmoc)ciW-NH$_2$ | 334 | (KFmoc)ciX-NH$_2$ | 412 |
| (KFmoc)ciG-NH$_2$ | 372 | | |
| (KFmoc)ciX-NH$_2$ | 412 | | |
| (KFmoc)ciV-NH$_2$ | 413 | | |
| (KFmoc)ciC-NH$_2$ | 537 | | |
| (KFmoc)cXX-NH$_2$ | 343 | | |
| (KFmoc)XXX-NH$_2$ | 770 | | |

| | IC$_{50}$ ($\mu$g/m) |
|---|---|
| (KFmoc)ci(KCBZ)-NH$_2$ | 78 |
| (KFmoc)ci(Nve)-NH$_2$ | 78 |
| (KFmoc)ci(Orn)-NH$_2$ | 115 |
| (KFmoc)ci(dOrn)-NH$_2$ | 121 |
| (KFmoc)ci(aAIB)-NH$_2$ | 183 |
| (KFmoc)ci(aABA)-NH$_2$ | 194 |
| (KFmoc)ci(Thiopro)-NH$_2$ | 197 |
| (KFmoc)ci(Hyp)-NH$_2$ | 205 |
| (KFmoc)ci(Nle)-NH$_2$ | 267 |
| (KFmoc)ci(KFmoc)-NH$_2$ | 356 |
| (KFmoc)ciX-NH$_2$ | 412 |

TABLE 18
HEMOLYTIC ACTIVITY OF (KFmoc)WKU-NH$_2$

| | HD$_{50}$ ($\mu$g/ml) | | HD$_{50}$ ($\mu$g/ml) |
|---|---|---|---|
| (KFmoc)WKW-NH$_2$ | 37 | (KFmoc)WKc-NH$_2$ | 25 |
| (KFmoc)WKC-NH$_2$ | 43 | (KFmoc)WKw-NH$_2$ | 32 |
| (KFmoc)WKL-NH$_2$ | 73 | (KFmoc)WKf-NH$_2$ | 126 |
| (KFmoc)WKM-NH$_2$ | 102 | (KFmoc)WKl-NH$_2$ | 166 |
| (KFmoc)WKF-NH$_2$ | 105 | (KFmoc)WKm-NH$_2$ | 178 |
| (KFmoc)WKV-NH$_2$ | 137 | (KFmoc)WKv-NH$_2$ | 181 |
| (KFmoc)WKI-NH$_2$ | 141 | (KFmoc)WKs-NH$_2$ | 296 |
| (KFmoc)WKY-NH$_2$ | 156 | (KFmoc)WKi-NH$_2$ | 296 |
| (KFmoc)WKN-NH$_2$ | 204 | (KFmoc)WKh-NH$_2$ | 313 |
| (KFmoc)WKS-NH$_2$ | 206 | (KFmoc)WKr-NH$_2$ | 324 |
| (KFmoc)WKH-NH$_2$ | 312 | (KFmoc)WKy-NH$_2$ | 368 |
| (KFmoc)WKT-NH$_2$ | 367 | (KFmoc)WKt-NH$_2$ | 435 |
| (KFmoc)WKA-NH$_2$ | 378 | (KFmoc)WKa-NH$_2$ | 437 |
| (KFmoc)WKR-NH$_2$ | 387 | (KFmoc)WKp-NH$_2$ | 437 |
| (KFmoc)WKG-NH$_2$ | 449 | (KFmoc)WKq-NH$_2$ | 483 |
| (KFmoc)WKK-NH$_2$ | 469 | | |
| (KFmoc)WKX-NH$_2$ | 209 | | |
| (KFmoc)WXX-NH$_2$ | 64 | | |

| | HD$_{50}$ ($\mu$g/ml) |
|---|---|
| (KFmoc)WK(NO$_2$F)-NH$_2$ | 67 |
| (KFmoc)WK(Nle)-NH$_2$ | 91 |
| (KFinoc)WK(Nve)-NH$_2$ | 98 |
| (KFmoc)WK(Thiopro)-NH$_2$ | 108 |
| (KFmoc)WK(dOrn)-NH$_2$ | 369 |
| (KEmoc)WK(MetO$_2$)-NH$_2$ | 437 |
| (KFmoc)WK(aAIB)-NH$_2$ | 447 |
| (KFmoc)WK(aABA)-NH$_2$ | 449 |

TABLE 19
HEMOLYTIC ACTIVITY OF (KFmoc)WYZ-NH$_2$

| | HD$_{50}$ ($\mu$g/ml) | | HD$_{50}$ ($\mu$g/ml) |
|---|---|---|---|

TABLE 19-continued
HEMOLYTIC ACTIVITY OF (KFmoc)WYZ-NH$_2$

| | | | |
|---|---|---|---|
| (KFmoc)WYR-NH$_2$ | 45 | (KFmoc)WYs-NH$_2$ | 27 |
| (KFmoc)WYK-NH$_2$ | 65 | (KFmoc)WYr-NH$_2$ | 31 |
| (KFmoc)WYT-NH$_2$ | 53 | (KFmoc)WYt-NH$_2$ | 37 |
| (KFmoc)WYP-NH$_2$ | 97 | (KFmoc)WYk-NH$_2$ | 62 |
| (KFmoc)WYH-NH$_2$ | 139 | (KFmoc)WYh-NH$_2$ | 73 |
| (KFmoc)WYC-NH$_2$ | 267 | (KFmoc)WYa-NH$_2$ | 74 |
| (KFmoc)WYG-NH$_2$ | 376 | (KFmoc)WYp-NH$_2$ | 76 |
| (KFmoc)WYX-NH$_2$ | 91 | (KFmoc)WYn-NH$_2$ | 257 |
| (KFmoc)WXX-NH$_2$ | 64 | | |

| | HD$_{50}$ ($\mu$g/ml) |
|---|---|
| (KFmoc)WY(Orn)-NH$_2$ | 62 |
| (KFmoc)WY(dOrn)-NH$_2$ | 67 |
| (KFmoc)WY(Hyp)-NH$_2$ | 81 |
| (KFmoc)WY(aABA)-NH$_2$ | 114 |
| (KFmoc)WY(Thiopro)-NH$_2$ | 488 |

TABLE 20
HEMOLYTIC ACTIVITY OF (KFmoc)WfZ-NH$_2$

| | HD$_{50}$ ($\mu$g/ml) | | HD$_{50}$ ($\mu$g/ml) |
|---|---|---|---|
| (KFmoc)WfP-NH$_2$ | 40 | (KFmoc)Wfw-NH$_2$ | 36 |
| (KFmoc)WfY-NH$_2$ | 42 | (KFmoc)Wfr-NH$_2$ | 42 |
| (KFmoc)WfR-NH$_2$ | 122 | (KFmoc)Wfp-NH$_2$ | 65 |
| (KFmoc)Wfl-NH$_2$ | 208 | (KFmoc)Wfl-NH$_2$ | 197 |
| (KFmoc)WfL-NH$_2$ | 294 | | |
| (KFmoc)WfX-NH$_2$ | 128 | | |
| (KFmoc)WXX-NH | 64 | | |

| | HD$_{50}$ ($\mu$g/m) |
|---|---|
| (KFmoc)Wf(Hyp)-NH$_2$ | 37 |
| (KFmoc)Wf(dOrn)-NH$_2$ | 42 |
| (KFmoc)Wf(MetO$_2$)-NH$_2$ | 44 |
| (KFmoc)Wf(Thiopro)-NH$_2$ | 45 |
| (KFmoc)Wf(KCBZ)-NH$_2$ | 52 |
| (KFmoc)Wf(Orn)-NH$_2$ | 64 |
| (KFmoc)Wf(aABA)-NH$_2$ | 241 |
| (KFmoc)Wf(Bala)-NH$_2$ | 360 |
| (KFmoc)Wf(aAIB)-NH$_2$ | 383 |

TABLE 21
HEMOLYTIC ACTIVITY OF (KFmoc)ciZ-NH$_2$

| | HD$_{50}$ ($\mu$g/ml) | | HD$_{50}$ ($\mu$g/ml) |
|---|---|---|---|
| (KFmoc)ciP-NH$_2$ | 27 | (KFmoc)cip-NH$_2$ | 39 |
| (KFmoc)ciT-NH$_2$ | 29 | (KFmoc)cit-NH$_2$ | 48 |
| (KFmoc)ciG-NH$_2$ | 35 | (KFmoc)cir-NH$_2$ | 48 |
| (KFmoc)ciQ-NH$_2$ | 40 | (KFmoc)cis-NH$_2$ | 49 |
| (KFmoc)ciS-NH$_2$ | 42 | (KFmoc)cik-NH$_2$ | 76 |
| (KFmoc)ciH-NH$_2$ | 47 | (KFmoc)cia-NH$_2$ | 77 |
| (KFmoc)ciR-NH$_2$ | 50 | (KFmoc)ciq-NH$_2$ | 195 |
| (KFmoc)ciA-NH$_2$ | 68 | (KFmoc)cin-NH$_2$ | 317 |
| (KFmoc)ciK-NH$_2$ | 79 | (KFmoc)cih-NH$_2$ | 382 |
| (KFmoc)ciL-NH$_2$ | 97 | (KFmoc)civ-NH$_2$ | 439 |
| (KFmoc)ciN-NH$_2$ | 116 | (KFmoc)cii-NH$_2$ | 443 |
| (KFmoc)ciW-NH$_2$ | 283 | | |
| (KFmoc)ciF-NH$_2$ | 295 | | |
| (KFmoc)ciM-NH$_2$ | 386 | | |
| (KFmoc)ciV-NH$_2$ | 391 | | |
| (KFmoc)ciC-NH$_2$ | 400 | | |
| (KFmoc)ciX-NH$_2$ | 92 | | |
| (KFmoc)cXX-NH$_2$ | 108 | | |

| | HD$_{50}$ ($\mu$g/ml) |
|---|---|
| (KFmoc)ci(aAIB)-NH$_2$ | 28 |
| (KFmoc)ci(aABA)-NH$_2$ | 29 |
| (KFmoc)ci(Bala)-NH$_2$ | 37 |
| (KFmoc)ci(Hyp)-NH$_2$ | 39 |

TABLE 21-continued

HEMOLYTIC ACTIVITY OF (KFmoc)ciZ-NH$_2$

| | |
|---|---|
| (KFmoc)ci(MetO$_2$)-NH$_2$ | 40 |
| (KFmoc)ci(KCBZ)-NH$_2$ | 53 |
| (KFmoc)ci(gABA)-NH$_2$ | 54 |
| (KFmoc)ci(Thiopro)-NH$_2$ | 58 |
| (KFmoc)ci(Orn)-NH$_2$ | 77 |
| (KFmoc)ci(dOrn)-NH$_2$ | 77 |
| (KFmoc)ci(Cys[ACM])-NH$_2$ | 84 |
| (KFmoc)ci(NO$_2$F)-NH$_2$ | 363 |

TABLE 22

Biological activity of Ac-RRWWCO-NH$_2$.

| Peptide sequence | IC$_{50}$ ($\mu$g/ml) against | | | | | % hemolysis at 100 $\mu$g/ml |
|---|---|---|---|---|---|---|
| | S. aureus | S. sanguis | E. coli | P. aeruginosa | C. albicans | |
| Ac-RRWWCA-NH$_2$ | 35–40 | 60–70 | 21–23 | 97–98 | 193–210 | 2.2 |
| Ac-RRWWCC-NH$_2$ | 47–63 | 92–94 | 54–68 | 86–88 | 162–166 | 9.5 |
| Ac-RRWWCD-NH$_2$ | >125 | >500 | >125 | >500 | >1000 | 0.3 |
| Ac-RRWWCE-NH$_2$ | >125 | >500 | >125 | 149 | 842–874 | 0.0 |
| Ac-RRWWCF-NH$_2$ | 10–14 | 14–22 | 20–21 | 42–45 | 70–97 | 3.3 |
| Ac-RRWWCG-NH$_2$ | 46–49 | 47–66 | 22–23 | 200 | 215–218 | 1.9 |
| Ac-RRWWCH-NH$_2$ | 26–28 | 53–62 | 20–28 | 59–65 | 69–107 | 0.0 |
| Ac-RRWWCI-NH$_2$ | 12–18 | 17–18 | 29–33 | 40–70 | 93–102 | 8.3 |
| Ac-RRWWCK-NH$_2$ | 17–18 | 38–42 | 17–21 | 150 | 100–110 | 0.5 |
| Ac-RRWWCL-NH$_2$ | 22–16 | 18–21 | 19–22 | 46–54 | 65–95 | 5.0 |
| Ac-RRWWCM-NH$_2$ | 13–20 | 13–22 | 23–27 | 93–103 | 96–112 | 15 |
| Ac-RRWWCN-NH$_2$ | 98–125 | 230 | 40–55 | 120 | 222–227 | 0.1 |
| Ac-RRWWCP-NH$_2$ | 49–50 | 190 | 19–27 | 200 | 217–222 | 0.0 |
| Ac-RRWWCQ-NH$_2$ | 52–98 | 230 | 41–42 | 60–65 | 223–230 | 0.0 |
| Ac-RRWWCR-NH$_2$ | 11–12 | 22–45 | 12–18 | 87–130 | 100–101 | 0.0 |
| Ac-RRWWCS-NH$_2$ | 41–44 | 54–59 | 20–21 | 290 | 211–213 | 1.8 |
| Ac-RRWWCT-NH$_2$ | 38–47 | 56–61 | 24–28 | 180 | 216–223 | 0.5 |
| Ac-RRWWCV-NH$_2$ | 19–21 | 41–46 | 17–18 | 33–44 | 103–174 | 0.0 |
| Ac-RRWWCW-NH$_2$ | 41–43 | 55–78 | 58–61 | 60–88 | 151–166 | 14 |
| Ac-RRWWCY-NH$_2$ | 12–28 | 59–60 | 20–21 | 97–110 | 184–212 | 5.8 |
| Ac-RRWWCX-NH$_2$ | 25–30 | 51–58 | 21–28 | 70–87 | 181–219 | 11 |
| Ac-RRWWXX-NH$_2$ | 32–33 | 36–51 | 31–37 | 93–125 | 195–204 | 1.6 |
| Ac-RRWXXX-NH$_2$ | 130 | 115 | 100 | >500 | 294–297 | 0.0 |
| Ac-RRXXXX-NH$_2$ | 1913 | >2500 | 935 | >500 | >2500 | 0.0 |

X represents an equimolar mixture of 19 of the 20 natural L-amino acids, cysteine being excluded. The greatest activities are represented in bold characters.

TABLE 23

Biological activity of all -D-amino acid peptides and of naturally occurring peptides

| Peptide sequence | IC$_{50}$ ($\mu$g/ml) against | | | | | % hemolysis at 100 $\mu$g/ml |
|---|---|---|---|---|---|---|
| | S. aureus | S. sanguis | E. coli | P. aeruginosa | C. albicans | |
| Ac-rrwwcr-NH$_2$ | 9–13 | 14–15 | 10–11 | 28–29 | 68–78 | 2.0 |
| Ac-rrwwcv-NH$_2$ | 16–19 | 7–8 | 9–10 | 58–88 | 107–119 | 10.0 |
| MagaininII-NH$_2$ | 32–64 | 143–235 | 72–98 | 150–200 | 41–42 | |
| Cecropin A | >500 | 337–400 | 1–2 | 5–6 | 81–88 | 0.0 |

EXAMPLE II

PEPTIDES HAVING ANTI-MELLITIN ACTIVITY

A. Positional Scanning Synthetic Peptide Combinatorial Libraries

A Positional Scanning Synthetic Peptide Combinational Library (SPCL) was prepared as described in C. Pinilla et al., Biotechniques, 13, p. 901 (1992). The six individual positional peptide libraries making up the positional scanning SPCL were prepared by previously described methods. Houghten et al., BioTechniques 13:412–421 (1992); Houghten et al., In T. Shiba and S. Sakakibara (Eds.), Peptide Chemistry, Protein Rsearch Foundation, Osaka 769–774 (1988); Houghten et al., Nature 354:84–86 (1991). Each of the six peptide libraries was composed of 18 peptide mixtures in which a single position was defined (represented by 0) with one of 18 of the 20 natural L-amino acids (cysteine and tryptophan were omitted), and the remaining five positions of the six-residue sequence were composed of mixtures (represented by X) of the same 18 amino acids. The six positional peptide libraries differed only in the location of the defined position. They were represented as Ac-O$_1$XXXXX-NH$_2$, Ac-XO$_2$XXXX-NH$_2$, Ac-XXO$_3$XXX-NH$_2$, Ac-XXXO$_4$XX-NH$_2$, Ac-XXXXO$_5$X-NH$_2$ and Ac-XXXXXO$_6$-NH$_2$ wherein 0 represented a fixed amino acid of choice and X represented an equimolar mixture of selected amino acids (108 peptide mixtures in total). Since each peptide mixture represented 1,889,568 ($18^5$) individual sequences, each of the six positional peptide libraries contained in total 34,012,224 (18 × 1,889, 568) different hexamers. Although each of the six positional SPCLs could be examined independently, this set of 108 peptide mixtures, when used in concert, yielded a positional scanning SPCL (PS-SPCL).

The peptide mixture resins which made up the PS-SPCL were prepared using chemical mixtures (i.e., a specific ratio of a mixture of amino acids. Houghten et al., In T. Shiba and S. Sakakibara (Eds.), Peptide Chemistry, Protein Rsearch Foundation, Osaka 769–774 (1988). Amino acid analysis, using the physically divided, coupled and recombined mixture resins as a control (Houghten et al., Nature 354:84–86 (1991) showed the presence of each amino acid in approximately equimolar concentration (±25%). The cleavage and extraction of peptide mixtures from the resin were carried out as described earlier for other SPCLs. Houghten et al.,

*BioTechniques* 13:412-421 (1992); Houghten et al., *Nature* 354:84-86 (1991).

B. Mellitin Inhibition Assay

Each assay was carried out in 96-well tissue culture plates. Four wells per plate contained 125 μl of a non-peptide control (1% Triton in deionized water), and four wells per plate contained 125 μl of a control blank, phosphate buffered saline (PBS). Uninhibited melittin was used as a comparative control. The controls served to detect possible contamination and to calculate the percent inhibition of each peptide. Human red blood cells (RBCs) were washed with PBS and centrifuged to separate them from the serum. RBCs were then resuspended in PBS to a final suspension of 0.5% RBCs. Peptides were added to the plate in duplicate and in 60 μl increments (5 μl of 10X PBS was added to salinate the aqueous peptides). The concentration necessary to inhibit 50% of the lysis of RBCs by melittin ($IC_{50}$), was determined by performing a serial two-fold dilution of the peptide ranging from 1000 μg/ml to 3.91 μg/ml. After peptides were prepared in the proper dilutions on the plate, 60 μl of a 30 μg/ml melittin solution in PBS were added to all wells containing peptide. 125 μl of the blood suspension was added to all the wells and the plates were incubated at 37° C. for one hour. They were then centrifuged at 2800 rpm for five minutes and the release of hemoglobin resulting from the cell lysis was determined by measuring the OD at 414 nm of 100 μl of the supernatant.

C. Results

An SPCL consisting of 400 different six-residue peptide mixtures (a total of 52,128,400 individual peptides) having acetylated N-terminals and amidated C-terminals was screened in a competition type hemolytic assay (i.e., competing melittin (7.5μg/ml–2.6μM); each individual peptide mixture was screened in the presence of 0.25% red blood cells (RBCs) in phosphate buffered saline). Each of the 400 peptide mixtures was represented by the formula $Ac-O_1O_2XXXX-NH_2$, where $O_1$ and $O_2$ represented each of the 20 natural L-amino acids and X represented an equimolar mixture of 19 of the 20 natural L-amino acids (cysteine omitted).

$Ac-IVXXXX-NH_2$ was one of the most active peptide mixtures found in this SPCL, and was followed to a final sequence as illustrated here. The four subsequent X positions were defined using an iterative process (R. A. Houghten et al., *Nature*, 354(1991). R. A. Houghten et al., *BioTechniques*, (1992) v. 13, pp. 412-421 in press.) involving synthesis, screening, and selection.

Hydrophobic character appears to be required for the peptide inhibitors of melittin. The activity of these peptides decreased as the concentration of melittin increased. These results suggest a mechanism of inhibition involving hydrophobic interactions between the peptides and melittin that prevent melittin from interacting with the membrane, and, in turn, lysing RBCs.

Tables 24 to 27 show the anti-melittin activity of various peptides. "X" refers to an equimolar mixture of the 19 naturally occuring L-amino acids (cysteine omitted).

TABLE 24

| Inhibition of melittin by $Ac-IVILTZ-NH_2$ | |
|---|---|
| | $IC_{50}$ (μg/ml) |
| Ac-IVILTM-NH$_2$ | 9 |
| Ac-IVILTF-NH$_2$ | 10 |

TABLE 24-continued

| Inhibition of melittin by $Ac-IVILTZ-NH_2$ | |
|---|---|
| | $IC_{50}$ (μg/ml) |
| Ac-IVILTL-NH$_2$ | 10 |
| Ac-IVILTQ-NH$_2$ | 11 |
| Ac-IVILTW-NH$_2$ | 11 |
| Ac-IVILTA-NH$_2$ | 13 |
| Ac-IVILTN-NH$_2$ | 14 |
| Ac-IVILTX-NH$_2$ | 16 |
| Ac-IVILTY-NH$_2$ | 18 |
| Ac-IVILTC-NH$_2$ | 19 |
| Ac-IVILTV-NH$_2$ | 21 |
| Ac-IVILTG-NH$_2$ | 22 |
| Ac-IVILTE-NH$_2$ | 24 |
| Ac-IVILTS-NH$_2$ | 36 |
| Ac-IVILTT-NH$_2$ | 44 |
| Ac-IVILTP-NH$_2$ | 49 |
| Ac-IVILTH-NH$_2$ | 56 |
| Ac-IVILTI-NH$_2$ | >250 |
| Ac-IVILTK-NH$_2$ | >250 |
| Ac-IVILTR-NH$_2$ | >250 |

TABLE 25

| Inhibition of melittin by $Ac-IVILLZ-NH_2$ | |
|---|---|
| | $IC_{50}$ (μg/ml) |
| Ac-IVILLW-NH$_2$ | 5 |
| Ac-IVILLE-NH$_2$ | 8 |
| Ac-IVILLQ-NH$_2$ | 9 |
| Ac-IVILLY-NH$_2$ | 10 |
| Ac-IVILLN-NH$_2$ | 13 |
| Ac-IVILLX-NH$_2$ | 13 |
| Ac-IVILLS-NH$_2$ | 15 |
| Ac-IVILLA-NH$_2$ | 15 |
| Ac-IVILLG-NH$_2$ | 17 |
| Ac-IVILLD-NH$_2$ | 18 |
| Ac-IVILLT-NH$_2$ | 18 |
| Ac-IVILLM-NH$_2$ | 20 |
| Ac-IVILLF-NH$_2$ | 21 |
| Ac-IVILLP-NH$_2$ | 26 |
| Ac-IVILLI-NH$_2$ | 26 |
| Ac-IVILLV-NH$_2$ | 70 |
| Ac-IVILLL-NH$_2$ | 89 |
| Ac-IVILLC-NH$_2$ | >250 |
| Ac-IVILLH-NH$_2$ | >250 |
| Ac-IVILLK-NH$_2$ | >250 |
| Ac-IVILLR-NH$_2$ | >250 |

TABLE 26

| Melittin inhibition by $Ac-IVIFFZ-NH_2$ | |
|---|---|
| | $IC_{50}$ (μg/ml) |
| Ac-IVIFFD-NH$_2$ | 10 |
| Ac-IVIFFE-NH$_2$ | 14 |
| Ac-IVIFFW-NH$_2$ | 16 |
| Ac-IVIFFN-NH$_2$ | 18 |
| Ac-IVIFFM-NH$_2$ | 21 |
| Ac-IVIFFY-NH$_2$ | 21 |
| Ac-IVIFFS-NH$_2$ | 21 |
| Ac-IVIFFX-NH$_2$ | 22 |
| Ac-IVIFFG-NH$_2$ | 22 |
| Ac-IVIFFT-NH$_2$ | 24 |
| Ac-IVIFFA-NH$_2$ | 25 |
| Ac-IVIFFQ-NH$_2$ | 26 |
| Ac-IVIFFV-NH$_2$ | 30 |
| Ac-IVIFFH-NH$_2$ | 30 |
| Ac-IVIFFP-NH$_2$ | 38 |
| Ac-IVIFFC-NH$_2$ | 72 |
| Ac-IVIFFI-NH$_2$ | 83 |
| Ac-IVIFFL-NH$_2$ | 111 |
| Ac-IVIFFF-NH$_2$ | 169 |
| Ac-IVIFFK-NH$_2$ | >250 |
| Ac-IVIFFR-NH$_2$ | >250 |

TABLE 27

Inhibition of melittin by individual peptides derived from PS-SPCL

| | IC$_{50}$ (μg/ml) |
|---|---|
| NDEIVI-NH$_2$ | 311 |
| NEEIVI-NH$_2$ | 364 |
| NDEIVF-NH$_2$ | 627 |
| NEEIVF-NH$_2$ | 905 |
| DDEITF-NH$_2$ | 1201 |
| Ac-FIIWCE-NH$_2$ | 3.4 |
| Ac-IIIWCE-NH$_2$ | 4.5 |
| Ac-FIIYCE-NH$_2$ | 4.7 |
| Ac-IQIYCE-NH$_2$ | 4.8 |
| Ac-IIIYFE-NH$_2$ | 4.9 |
| Ac-IIIWFE-NH$_2$ | 5.4 |
| Ac-FIIWFE-NH$_2$ | 5.4 |
| Ac-IQIWCE-NH$_2$ | 5.6 |
| Ac-FIIYFE-NH$_2$ | 6.8 |
| Ac-FQIWFE-NH$_2$ | 8.2 |
| Ac-FQIWCE-NH$_2$ | 9.4 |
| Ac-IIIYCE-NH$_2$ | 12 |
| Ac-FQIYCE-NH$_2$ | 14 |
| Ac-IQIYFE-NH$_2$ | 17 |
| Ac-FQIYFE-NH$_2$ | 19 |
| Ac-IQIWFE-NH$_2$ | 21 |
| Ac-IDIWCK-NH$_2$ | 106 |
| Ac-FDIWFK-NH$_2$ | 115 |
| Ac-FDIWFE-NH$_2$ | 166 |
| Ac-FDIYCE-NH$_2$ | 190 |
| Ac-IDIYCE-NH$_2$ | 287 |
| Ac-IDIYFE-NH$_2$ | 298 |
| Ac-FIIYFK-NH$_2$ | 365 |
| Ac-IDIYFK-NH$_2$ | 770 |
| Ac-IDIWCE-NH$_2$ | 801 |
| Ac-FDIYFE-NH$_2$ | 922 |
| Ac-IQIYCK-NH$_2$ | 1061 |
| Ac-FIIWFK-NH$_2$ | 1298 |
| Ac-MILWIE-NH$_2$ | 11 |
| Ac-VIQQFV-NH$_2$ | 16 |
| Ac-WIQIFI-NH$_2$ | 22 |

EXAMPLE III

ALL D-AMINO ACID PEPTIDES HAVING TRYPSIN INHIBITING ACTIVITY

A. Synthetic Peptide Libraries

A positional scanning synthetic peptide combinatorial library (PS-SPCL), represented by the formulas Ac-oxxxxx-NH$_2$, Ac-xoxxxx-NH$_2$, Ac-xxoxxx-NH$_2$, Ac-xxxoxx-NH$_2$, Ac-xxxxox-NH$_2$ and Ac-xxxxxo-NH$_2$, was generated as described earlier (C. Pinilla, et. al., (1992) BioTechniques 13:901–905). Each of the sequences listed above represents twenty peptide mixtures in which o represents positions occupied by one of the 19 D-amino acids or glycine, and x represents positions occupied by a mixture of 18 of the 19 D-amino acids (cysteine excluded), and glycine. The x positions were incorporated by coupling of a mixture of 18 of the 19 D-amino acids (cysteine excluded) and glycine. The molar ratio of the amino acids in the mixture was the same as established for the coupling of mixtures of L-amino acids (Dooley, C. & Houghten, R. A. (1993) Life Science 52:1509–1517).

The peptide mixtures represented by the formulas Ac-ryoxxx-NH$_2$, Ac-ryroxx-NH$_2$ and Ac-ryrpox-NH$_2$ were synthesized using the DCR (divide, couple, recombine) process (Houghten, R. A., et al., Nature 354:84–86 (1991)). The individual peptides represented by the formula Ac-ryrpwo-NH$_2$ were synthesized using the method of simultaneous multiple peptide synthesis (SMPS) (Houghten, R. A. (1985) Proc.Natl.Acad. Sci. U.S.A. 82:5131–135; U.S. Pat. No. 4,631,211).

B. Trypsin Inhibition Assay

The assay was performed in a 96-well assay plate, 15 μl trypsin (from bovine pancreas, 8,600 units/mg solid) solution (0.05 mg/ml 0.02 M HCl), 50 μl peptide solution (1 to 3 mM in water), and 100 μl 0.1 M Tris-buffer containing 25 mM CaCl$_2$ (pH 7.8) were mixed in the wells of the assay plate. After incubation for 30 minutes, 100 μl substrate solution (N$^\alpha$-benzoyl-DL-arginine-p-nitroanilide, 2.3 mM in water) was added. After 30 minutes, absorbances were read at 405 nm using a Titertek multichannel photometer, and expressed as a percentage of the control (well without peptide). The values obtained with serial dilutions of the peptide solutions were used to determine the IC$_{50}$ values (concentration neccessary for 50% inhibition).

C. Results

The 20 individual peptides, represented by the formula Ac-ryrpwo-NH$_2$, were synthesized and screened. The peptides with the highest trypsin inhibiting activity (IC$_{50}$ less than 150 μM) are listed in Table 28.

TABLE 28

Trypsin inhibiting activity of all D-amino acid peptides with IC$_{50}$ less than 150 μM

| peptide | IC$_{50}$ [μM] |
|---|---|
| Ac-ryrpwp-NH$_2$ | 62 |
| Ac-ryrpww-NH$_2$ | 125 |
| Ac-ryrpwv-NH$_2$ | 131 |
| Ac-ryrpwc-NH$_2$ | 135 |
| Ac-ryrpwt-NH$_2$ | 142 |

Although the invention has been described with reference to the presently-preferred embodiments, it should be understood that various modifications can be made without departing from the spirit of the invention. Accordingly, the invention is limited only by the following claims.

We claim:

1. A peptide having the formula (KFmoc)WZZ-NH$_2$ [SEQ ID NO: 2].

2. A peptide of claim 1 having the formula (KFmoc)WKZ-NH$_2$ [SEQ ID NO: 3].

3. A peptide of claim 1 having the formula (KFmoc)WYZ-NH$_2$ [SEQ ID NO: 4].

4. A peptide of claim 1 having the formula (KFmoc)WfZ-NH$_2$.

5. A peptide having anti-microbial activity and having the formula (KFmoc)ciZ-NH$_2$ wherein Z is an amino acid.

6. A peptide of any of claims 1-5 having HD$_{50}$ greater than than 100 μgms/ml.

7. A composition comprising a peptide of claim 1 or 5 in an acceptable carrier.

8. A pharmaceutical composition comprising a peptide of claim 1 or 5 in a pharmaceutically acceptable carrier.

9. A method of treating a subject having a microbial infection comprising the step of administering to the subject a therapeutically effective amount of a pharmaceutical composition of claim 8, wherein the peptide has HD$_{50}$ greater than 100 μgms/ml.

10. A method of inhibiting the growth of a microorganism comprising the step of contacting the microorganism with an effective amount of a peptide of claim 1 or 5.

* * * * *

UNITED STATES PATENT AND TRADEMARK OFFICE
CERTIFICATE OF CORRECTION

PATENT NO. : 5,440,016

DATED : August 8, 1995

INVENTOR(S) : Blondelle and Houghten

It is certified that error appears in the above-indentified patent and that said Letters Patent is hereby corrected as shown below:

On the title page, item [54] and Column 1, The title needs to be changed from "Peptides of the Formula (Kfmoc)ZZZ and Their Uses" to --Antimicrobial Tetrapeptide of the Formula (Kfmoc)ZZZ--.

In column 1, line 26, please delete "mumber" and replace therefor with --number--.

In column 2, line 22, please insert a space between "10]" and "or".

In column 2, line 42, between "z" and "a" please insert --is--.

In column 4, line 35, please delete "amido" and insert therefor --amino--.

In column 5, line 1, please delete "HD50" and replace therefor with --$HD_{50}$--.

In column 5, the 30th line in the second table, please delete "(Kfmoc)WK(gABA)-$NH_2$".

In column 6, the 36th line in the table, please delete "(Kfmoc)WfK-$NH_2$".

In column 9, line 46, please delete "provide" and insert therefor --provides--.

In column 12, line 67, please delete "Z4" and insert therefor --$Z_4$--.

In column 13, line 1, please delete "introducion" and insert therefor --introduction--.

UNITED STATES PATENT AND TRADEMARK OFFICE
CERTIFICATE OF CORRECTION

PATENT NO. : 5,440,016
DATED : August 8, 1995
INVENTOR(S) : Blondelle and Houghten It is certified that error appears in the above-indentified patent and that said Letters Patent is hereby corrected as shown below:

In column 14, line 6, please delete "lose." and replace therefor with --lose"--.

In column 15, line 47, please delete "(182)" and replace therefor with --($18^2$)--.

In column 15, line 24, please delete "82.," and replace therefor with --82,--.

In column 16, line 37, please delete the first "$10^{-4}$)" and replace therefor with --$10^{-3}$--.

In column 17, line 42, please delete "and" and replace therefor with --an--.

In column 25, Table 14, the 12th line from the bottom, please delete "(Kfmoc)WY(Orn)-$NH_2$" and replace therefor with --(Kfmoc)WK(Orn)-$NH_2$--.

In column 29, line 63, please delete "Rsearch" and replace therefor with --Research--.

UNITED STATES PATENT AND TRADEMARK OFFICE
CERTIFICATE OF CORRECTION

PATENT NO.  : 5,440,016
DATED       : August 8, 1995
INVENTOR(S) : Blondelle and Houghten It is certified that error appears in the above-indentified patent and that said Letters Patent is hereby corrected as shown below:

In column 30, line 52, please delete the space between "1,889," and "568)".

In column 30, line 61, please delete "Rsearch" and replace therefor with --Research--.

In column 34, line 14, please delete "135" and replace therefor with --5135--.

In claim 6, column 45, line 51, please delete the first "than".

Signed and Sealed this

Twentieth Day of August, 1996

BRUCE LEHMAN

Attest:

Attesting Officer

Commissioner of Patents and Trademarks

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
        ( A ) NAME/KEY: Modified-site ( B ) LOCATION: 1
( D ) OTHER INFORMATION: /label=Xaa
/ note="Xaa=KFmoc"

( i x ) FEATURE:
( A ) NAME/KEY: Modified-site
( B ) LOCATION: 2..4
( D ) OTHER INFORMATION: /label=Xaa
/ note="Xaa=any amino acid"

( i x ) FEATURE:
( A ) NAME/KEY: Modified-site
( B ) LOCATION: 4
( D ) OTHER INFORMATION: /note="C-terminal amino acid is amidated"

( x i ) SEQUENCE DESCRIPTION: SEQ ID NO:1:

Xaa Xaa Xaa Xaa
1

( 2 ) INFORMATION FOR SEQ ID NO:2:

( i ) SEQUENCE CHARACTERISTICS:
( A ) LENGTH: 4 amino acids
( B ) TYPE: amino acid
( D ) TOPOLOGY: linear ( i x ) FEATURE:
( A ) NAME/KEY: Modified-site
( B ) LOCATION: 1
( D ) OTHER INFORMATION: /label=Xaa
/ note="Xaa=KFmoc"

( i x ) FEATURE:
( A ) NAME/KEY: Modified-site
( B ) LOCATION: 3..4
( D ) OTHER INFORMATION: /label=Xaa
/ note="Xaa=any amino acid"

( i x ) FEATURE:
( A ) NAME/KEY: Modified-site
( B ) LOCATION: 4
( D ) OTHER INFORMATION: /note="C-terminal amino acid is amidated"

( x i ) SEQUENCE DESCRIPTION: SEQ ID NO:2:

Xaa Trp Xaa Xaa
1

( 2 ) INFORMATION FOR SEQ ID NO:3:

( i ) SEQUENCE CHARACTERISTICS:
( A ) LENGTH: 4 amino acids
( B ) TYPE: amino acid
( D ) TOPOLOGY: linear ( i x ) FEATURE:
( A ) NAME/KEY: Modified-site
( B ) LOCATION: 1
( D ) OTHER INFORMATION: /label=Xaa
/ note="Xaa=KFmoc"

( i x ) FEATURE:
( A ) NAME/KEY: Modified-site
( B ) LOCATION: 4
( D ) OTHER INFORMATION: /label=Xaa
/ note="Xaa=any amino acid"

( i x ) FEATURE:
( A ) NAME/KEY: Modified-site
( B ) LOCATION: 4
( D ) OTHER INFORMATION: /note="C-terminal amino acid is amidated"

( x i ) SEQUENCE DESCRIPTION: SEQ ID NO:3:

Xaa Trp Lys Xaa
1

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
        ( A ) NAME/KEY: Modified-site
        ( B ) LOCATION: 1
        ( D ) OTHER INFORMATION: /label=Xaa
            / note="Xaa=KFmoc"

( i x ) FEATURE:
        ( A ) NAME/KEY: Modified-site
        ( B ) LOCATION: 4
        ( D ) OTHER INFORMATION: /label=Xaa
            / note="Xaa=any amino acid"

( i x ) FEATURE:
        ( A ) NAME/KEY: Modified-site
        ( B ) LOCATION: 4
        ( D ) OTHER INFORMATION: /note="C-terminal amino acid is
            amidated"

( x i ) SEQUENCE DESCRIPTION: SEQ ID NO:4:

Xaa   Trp   Tyr   Xaa
    1

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Modified-site
        ( B ) LOCATION: 1
        ( D ) OTHER INFORMATION: /note="N-terminal amino acid is
            acetylated"

( i x ) FEATURE:
        ( A ) NAME/KEY: Modified-site
        ( B ) LOCATION: 5..6
        ( D ) OTHER INFORMATION: /label=Xaa
            / note="Xaa=any amino acid"

( i x ) FEATURE:
        ( A ) NAME/KEY: Modified-site
        ( B ) LOCATION: 6
        ( D ) OTHER INFORMATION: /note="C-terminal amino acid is
            amidated"

( x i ) SEQUENCE DESCRIPTION: SEQ ID NO:5:

Arg   Arg   Trp   Trp   Xaa   Xaa
    1                                5

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Modified-site
        ( B ) LOCATION: 1
        ( D ) OTHER INFORMATION: /note="N-terminal amino acid is
            acetylated"

( i x ) FEATURE:
        ( A ) NAME/KEY: Modified-site
        ( B ) LOCATION: 6
        ( D ) OTHER INFORMATION: /label=Xaa
            / note="Xaa=any amino acid"

( i x ) FEATURE:
    ( A ) NAME/KEY: Modified-site
    ( B ) LOCATION: 6
    ( D ) OTHER INFORMATION: /note="C-terminal amino acid is
        amidated"

( x i ) SEQUENCE DESCRIPTION: SEQ ID NO:6:

```
Arg  Arg  Trp  Trp  Cys  Xaa
 1                 5
```

( 2 ) INFORMATION FOR SEQ ID NO:7:

( i ) SEQUENCE CHARACTERISTICS:
        ( A ) LENGTH: 26 amino acids
        ( B ) TYPE: amino acid
        ( D ) TOPOLOGY: linear ( i x ) FEATURE:
        ( A ) NAME/KEY: Modified-site
        ( B ) LOCATION: 26
        ( D ) OTHER INFORMATION: /note="C-terminal amino acid is
            amidated"

( x i ) SEQUENCE DESCRIPTION: SEQ ID NO:7:

```
Gly  Ile  Gly  Ala  Val  Leu  Lys  Val  Leu  Thr  Thr  Gly  Leu  Pro  Ala  Leu
 1                 5                           10                          15

Ile  Ser  Trp  Ile  Lys  Arg  Lys  Arg  Gln  Gln
                20                      25
```

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Modified-site
        ( B ) LOCATION: 1
        ( D ) OTHER INFORMATION: /note="N-terminal amino acid is
            acetylated"

( i x ) FEATURE:
        ( A ) NAME/KEY: Modified-site
        ( B ) LOCATION: 5..6
        ( D ) OTHER INFORMATION: /label=Xaa
            / note="Xaa=any amino acid"

( i x ) FEATURE:
        ( A ) NAME/KEY: Modified-site
        ( B ) LOCATION: 6
        ( D ) OTHER INFORMATION: /note="C-terminal amino acid is
            amidated"

( x i ) SEQUENCE DESCRIPTION: SEQ ID NO:8:

```
Ile  Val  Ile  Leu  Xaa  Xaa
 1                 5
```

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Modified-site
        ( B ) LOCATION: 1
        ( D ) OTHER INFORMATION: /note="N-terminal amino acid is
            acetylated"

( i x ) FEATURE:
        ( A ) NAME/KEY: Modified-site
        ( B ) LOCATION: 6

( D ) OTHER INFORMATION: /label=Xaa
/ note="Xaa=any amino acid"

( i x ) FEATURE:
( A ) NAME/KEY: Modified-site
( B ) LOCATION: 6
( D ) OTHER INFORMATION: /note="C-terminal amino acid is
amidated"

( x i ) SEQUENCE DESCRIPTION: SEQ ID NO:9:

Ile Val Ile Leu Thr Xaa
1               5

( 2 ) INFORMATION FOR SEQ ID NO:10:

( i ) SEQUENCE CHARACTERISTICS:
( A ) LENGTH: 6 amino acids
( B ) TYPE: amino acid
( D ) TOPOLOGY: linear ( i x ) FEATURE:
( A ) NAME/KEY: Modified-site
( B ) LOCATION: 1
( D ) OTHER INFORMATION: /note="N-terminal amino acid is
acetylated"

( i x ) FEATURE:
( A ) NAME/KEY: Modified-site
( B ) LOCATION: 6
( D ) OTHER INFORMATION: /label=Xaa
/ note="Xaa=any amino acid"

( i x ) FEATURE:
( A ) NAME/KEY: Modified-site
( B ) LOCATION: 6
( D ) OTHER INFORMATION: /note="C-terminal amino acid is
amidated"

( x i ) SEQUENCE DESCRIPTION: SEQ ID NO:10:

Ile Val Ile Leu Leu Xaa
1               5

( 2 ) INFORMATION FOR SEQ ID NO:11:

( i ) SEQUENCE CHARACTERISTICS:
( A ) LENGTH: 6 amino acids
( B ) TYPE: amino acid
( D ) TOPOLOGY: linear ( i x ) FEATURE:
( A ) NAME/KEY: Modified-site
( B ) LOCATION: 1
( D ) OTHER INFORMATION: /note="N-terminal amino acid is
acetylated"

( i x ) FEATURE:
( A ) NAME/KEY: Modified-site
( B ) LOCATION: 6
( D ) OTHER INFORMATION: /label=Xaa
/ note="Xaa=any amino acid"

( i x ) FEATURE:
( A ) NAME/KEY: Modified-site
( B ) LOCATION: 6
( D ) OTHER INFORMATION: /note="C-terminal amino acid is
amidated"

( x i ) SEQUENCE DESCRIPTION: SEQ ID NO:11:

Ile Val Ile Phe Phe Xaa
1               5

( 2 ) INFORMATION FOR SEQ ID NO:12:

( i ) SEQUENCE CHARACTERISTICS:
( A ) LENGTH: 6 amino acids
( B ) TYPE: amino acid -continued ( D ) TOPOLOGY: linear ( i x ) FEATURE:
                    ( A ) NAME/KEY: Modified-site
                    ( B ) LOCATION: 1
                    ( D ) OTHER INFORMATION: /note="N-terminal amino acid is
                            acetylated"

( i x ) FEATURE:
                    ( A ) NAME/KEY: Modified-site
                    ( B ) LOCATION: 1
                    ( D ) OTHER INFORMATION: /label=Xaa
                            / note="Xaa=Phe or Ile"

( i x ) FEATURE:
                    ( A ) NAME/KEY: Modified-site
                    ( B ) LOCATION: 2
                    ( D ) OTHER INFORMATION: /label=Xaa
                            / note="Xaa=Ile, Gln or Asp"

( i x ) FEATURE:
                    ( A ) NAME/KEY: Modified-site
                    ( B ) LOCATION: 4
                    ( D ) OTHER INFORMATION: /label=Xaa
                            / note="Xaa=Trp or Tyr"

( i x ) FEATURE:
                    ( A ) NAME/KEY: Modified-site
                    ( B ) LOCATION: 5
                    ( D ) OTHER INFORMATION: /label=Xaa
                            / note="Xaa=Cys or Phe"

( i x ) FEATURE:
                    ( A ) NAME/KEY: Modified-site
                    ( B ) LOCATION: 6
                    ( D ) OTHER INFORMATION: /label=Xaa
                            / note="Xaa=Glu or Lys"

( i x ) FEATURE:
                    ( A ) NAME/KEY: Modified-site
                    ( B ) LOCATION: 6
                    ( D ) OTHER INFORMATION: /note="C-terminal amino acid is
                            amidated"

( x i ) SEQUENCE DESCRIPTION: SEQ ID NO:12:

Xaa  Xaa  Ile  Xaa  Xaa  Xaa
        1                   5

( 2 ) INFORMATION FOR SEQ ID NO:13:

( i ) SEQUENCE CHARACTERISTICS:
                    ( A ) LENGTH: 6 amino acids
                    ( B ) TYPE: amino acid
                    ( D ) TOPOLOGY: linear ( i x ) FEATURE:
                    ( A ) NAME/KEY: Modified-site
                    ( B ) LOCATION: 1
                    ( D ) OTHER INFORMATION: /note="N-terminal amino acid is
                            acetylated"

( i x ) FEATURE:
                    ( A ) NAME/KEY: Modified-site
                    ( B ) LOCATION: 6
                    ( D ) OTHER INFORMATION: /note="C-terminal amino acid is
                            amidated"

( x i ) SEQUENCE DESCRIPTION: SEQ ID NO:13:

Met  Ile  Leu  Trp  Ile  Glu
        1                   5

( 2 ) INFORMATION FOR SEQ ID NO:14:

( i ) SEQUENCE CHARACTERISTICS:
                    ( A ) LENGTH: 6 amino acids
                    ( B ) TYPE: amino acid
                    ( D ) TOPOLOGY: linear (ix) FEATURE:
  (A) NAME/KEY: Modified-site
  (B) LOCATION: 1
  (D) OTHER INFORMATION: /note="N-terminal amino acid is acetylated"

(ix) FEATURE:
  (A) NAME/KEY: Modified-site
  (B) LOCATION: 6
  (D) OTHER INFORMATION: /note="C-terminal amino acid is amidated"

(xi) SEQUENCE DESCRIPTION: SEQ ID NO:14:

Val Ile Gln Gln Phe Val
 1               5

(2) INFORMATION FOR SEQ ID NO:15:

(i) SEQUENCE CHARACTERISTICS:
    (A) LENGTH: 6 amino acids
    (B) TYPE: amino acid
    (D) TOPOLOGY: linear (ix) FEATURE:
    (A) NAME/KEY: Modified-site
    (B) LOCATION: 1
    (D) OTHER INFORMATION: /note="N-terminal amino acid is acetylated"

(ix) FEATURE:
    (A) NAME/KEY: Modified-site
    (B) LOCATION: 6
    (D) OTHER INFORMATION: /note="C-terminal amino acid is amidated"

(xi) SEQUENCE DESCRIPTION: SEQ ID NO:15:

Trp Ile Gln Ile Phe Ile
 1               5